US00RE46374E

(19) United States
(12) Reissued Patent
Schaub et al.

(10) Patent Number: US RE46,374 E
(45) Date of Reissued Patent: Apr. 25, 2017

(54) PROCESS FOR PREPARING DI-, TRI- AND POLYAMINES BY HOMOGENEOUSLY CATALYZED ALCOHOL AMINATION

(71) Applicant: BASF SE, Ludwigshafen (DE)

(72) Inventors: Thomas Schaub, Neustadt (DE); Boris Buschhaus, Mannheim (DE); Marion Kristina Da Silva, Mannheim (DE); Mathias Schelwies, Heidelberg (DE); Rocco Paciello, Bad Duerkheim (DE); Johann-Peter Melder, Boehl-Iggelheim (DE); Martin Merger, Frankenthal (DE)

(73) Assignee: BASF SE, Ludwigshafen (DE)

(21) Appl. No.: 15/051,391

(22) Filed: Feb. 23, 2016

Related U.S. Patent Documents

Reissue of:
(64) Patent No.: 8,912,361
Issued: Dec. 16, 2014
Appl. No.: 13/415,466
Filed: Mar. 8, 2012

U.S. Applications:
(60) Provisional application No. 61/450,157, filed on Mar. 8, 2011.

(51) Int. Cl.

| | |
|---|---|
| ***C07C 213/02*** | (2006.01) |
| ***C07D 307/52*** | (2006.01) |
| ***C07C 209/16*** | (2006.01) |
| ***C07C 211/10*** | (2006.01) |
| ***C07C 217/08*** | (2006.01) |
| ***C07C 215/08*** | (2006.01) |
| ***C07C 211/09*** | (2006.01) |
| ***C07C 211/18*** | (2006.01) |
| ***C07C 215/20*** | (2006.01) |
| ***C07C 211/12*** | (2006.01) |
| ***C07D 223/04*** | (2006.01) |
| ***C07D 205/04*** | (2006.01) |
| ***C07D 207/02*** | (2006.01) |
| ***C07D 207/20*** | (2006.01) |
| ***C07D 211/06*** | (2006.01) |
| ***C07D 295/027*** | (2006.01) |

(52) U.S. Cl.
CPC ..... *C07C 209/16* (2013.01); *C07C 211/09* (2013.01); *C07C 211/10* (2013.01); *C07C 211/12* (2013.01); *C07C 211/18* (2013.01); *C07C 213/02* (2013.01); *C07C 215/08* (2013.01); *C07C 215/20* (2013.01); *C07C 217/08* (2013.01); *C07D 205/04* (2013.01); *C07D 207/02* (2013.01); *C07D 207/20* (2013.01); *C07D 211/06* (2013.01); *C07D 223/04* (2013.01); *C07D 295/027* (2013.01); *C07D 307/52* (2013.01)

(58) Field of Classification Search
CPC ... C07C 209/16; C07C 213/02; C07C 217/08; C07C 215/08; C07C 215/20; C07C 211/09; C07C 211/10; C07C 211/12; C07C 211/18; C07C 2101/14; C07D 223/04; C07D 205/04; C07D 207/02; C07D 207/20; C07D 211/06; C07D 295/027; C07D 307/52
See application file for complete search history.

(56) References Cited

U.S. PATENT DOCUMENTS

| | | | | |
|---|---|---|---|---|
| 3,275,554 | A | 9/1966 | Wagenaar | |
| 3,708,539 | A | 1/1973 | Fenton | |
| 4,709,034 | A | 11/1987 | Marsella | |
| 4,832,702 | A | 5/1989 | Kummer et al. | |
| 4,855,425 | A | 8/1989 | Marsella | |
| 4,912,260 | A | 3/1990 | Dobson et al. | |
| 4,942,261 | A | 7/1990 | Ishimura et al. | |
| 5,530,127 | A | 6/1996 | Reif et al. | |
| 7,754,922 | B2 | 7/2010 | Kubanek et al. | |
| 8,642,811 | B2 | 2/2014 | Baumann et al. | |
| 8,835,691 | B2 | 9/2014 | Klasovsky et al. | |
| 8,927,773 | B2 | 1/2015 | Klasovsky et al. | |
| 2009/0275781 | A1 | 11/2009 | Kubanek et al. | |
| 2010/0022746 | A1 | 1/2010 | Williams | |
| 2010/0331573 | A1 | 12/2010 | Schaub et al. | |
| 2011/0137029 | A1 | 6/2011 | Kubanek et al. | |
| 2011/0137030 | A1 | 6/2011 | Kubanek et al. | |
| 2011/0152525 | A1* | 6/2011 | Milstein et al. | 546/10 |
| 2011/0294977 | A1 | 12/2011 | Schaub et al. | |
| 2012/0004464 | A1 | 1/2012 | Huyghe et al. | |
| 2012/0071692 | A1 | 3/2012 | Ahrens et al. | |
| 2012/0095221 | A1 | 4/2012 | Wigbers et al. | |
| 2012/0157715 | A1 | 6/2012 | Pape et al. | |
| 2012/0203033 | A1* | 8/2012 | Baumann et al. | 564/480 |

FOREIGN PATENT DOCUMENTS

| | | |
|---|---|---|
| AU | 2009280778 | 2/2010 |
| AU | 2009280778 A1 | 2/2010 |

(Continued)

OTHER PUBLICATIONS

M. Haniti S. A. Harnid, et al., "Ruthenium-Catalyzed N-Alkylation of Amines and Sulfonamides Using Borrowing Hydrogen Methodology", J. Am. Chem. Soc., 131, 2009, pp. 1766-1774.

(Continued)

*Primary Examiner* — Jerry D Johnson
(74) *Attorney, Agent, or Firm* — Oblon, McClelland, Maier & Neustadt, L.L.P.

(57) ABSTRACT

Process for preparing primary amines which have at least one functional group of the formula (—$CH_2$—$NH_2$) and at least one further primary amino group by alcohol amination of starting materials having at least one functional group of the formula (—$CH_2$—OH) and at least one further functional group (—X), where (—X) is selected from among hydroxyl groups and primary amino groups, by means of ammonia with elimination of water, wherein the reaction is carried out homogeneously catalyzed in the presence of at least one complex catalyst comprising at least one element selected from groups 8, 9 and 10 of the Periodic Table and also at least one donor ligand.

20 Claims, No Drawings

(56) References Cited

FOREIGN PATENT DOCUMENTS

| | | | |
|---|---|---|---|
| CA | 1287630 | | 8/1991 |
| DE | 2 125 039 | | 12/1971 |
| DE | 36 11 230 | | 10/1987 |
| DE | 36 11 230 | A1 | 10/1987 |
| DE | 10 2010 040 427 | | 3/2012 |
| DE | 10 2010 040 427 | A1 | 3/2012 |
| EP | 0 234 401 | | 9/1987 |
| EP | 0 234 401 | A1 | 9/1987 |
| EP | 0 239 934 | | 10/1987 |
| EP | 0 239 934 | A2 | 10/1987 |
| EP | 0 320 269 | | 6/1989 |
| EP | 0 320 269 | A2 | 6/1989 |
| EP | 0 696 572 | | 2/1996 |
| EP | 0 696 572 | A1 | 2/1996 |
| JP | 63-255251 | | 10/1988 |
| JP | 2012-162525 | | 8/2012 |
| JP | 2013-538816 | | 10/2013 |
| JP | 2014-505029 | | 2/2014 |
| WO | WO 03/051508 | | 6/2003 |
| WO | WO 03/051508 | A1 | 6/2003 |
| WO | WO 2008/006752 | | 1/2008 |
| WO | WO 2008/006752 | A1 | 1/2008 |
| WO | WO 2010/018570 | | 2/2010 |
| WO | WO 2010/018570 | A1 | 2/2010 |
| WO | WO 2011/067199 | | 6/2011 |
| WO | WO 2011/067199 | A1 | 6/2011 |
| WO | WO 2011/067200 | | 6/2011 |
| WO | WO 2011/067200 | A1 | 6/2011 |
| WO | WO 2011/082967 | | 7/2011 |
| WO | WO 2011/082967 | A1 | 7/2011 |
| WO | WO 2011/151268 | | 12/2011 |
| WO | WO 2011/151268 | A1 | 12/2011 |
| WO | WO 2011/157710 | | 12/2011 |
| WO | WO 2011/157710 | A1 | 12/2011 |
| WO | WO 2012/000952 | | 1/2012 |
| WO | WO 2012/000952 | A1 | 1/2012 |
| WO | WO 2012/034933 | | 3/2012 |
| WO | WO 2012/034933 | A1 | 3/2012 |
| WO | WO 2012/049101 | | 4/2012 |
| WO | WO 2012/049101 | A1 | 4/2012 |

OTHER PUBLICATIONS

Chidambaram Gunanathan, et al., "Selective Synthesis of Primary Amines Directly from Alcohols and Ammonia", Angew. Chem. Int. Ed., 47, 2008, pp. 8661-8664.

Ryoko Kawahara, et al., "Multialkylation of Aqueous Ammonia with Alcohols Catalyzed by Water-Soluble Cp*Ir-Ammine Complexes", J. Am. Chem. Soc., 132, D01:10.10211ja107274w, 2010, 15108-15111.

Ken-ichi Fujita, et al., "Cp'Ir Complex-Catalyzed N-Heterocyclization of Primary Amines with Diols: A New Catalytic System for Environmentally Benign Synthesis of Cyclic Amines", Organic Letters, vol. 6, No. 20, 2004, pp. 3525-3528.

Alessandro Del Zotto, et al., "Cyclopentadienyl Ru" Complexes as Highly Efficient Catalysts for the N-Methylation of Alkylamines by Methanol", Eur. J. Inorg. Chem., 2004, pp. 524-529.

Benoit Blank, et al., "An Efficient Method for the Selective Iridium-Catalyzed Monoalkylation of (Hetero)aromatic Amines with Primary Alcohols", Adv. Synth. Catal., 350, 2008, pp. 749-758.

Ana Martinez-Asencio, et al., "N-Alkylation of poor nucleophilic amine and sulfonamide derivatives with alcohols by a hydrogen autotransfer process catalyzed by copper(II) acetate", Tetrahedron Letters 51, 2010, pp. 325-327.

J. A. Marsella, "Homogeneously Catalyzed Synthesis of /3-Amino Alcohols and Vicinal Diamines from Ethylene Glycol and 1,2-Propanediol", J. Org. Chem, 52, 1987, pp. 467-468.

Keun-Tae Huh, "Ruthenium Complex Catalyzed Synthesis of Diamino Compounds from a, w-Diols and Secondary Amines", Bull. Korean Chem. Soc., vol. 11, No. 1, 1990, pp. 45-49.

Sebastian Bahn, et al., "Ruthenium-catalyzed Selective Monoamination of Vicinal Diols", ChemSusChem, 2, 2009, pp. 551-557.

John A. Marsella, "Ruthenium catalyzed reactions of ethylene glycol with primary amines: steric factors and selectivity control", Journal of Organometallic Chemistry, 407, 1991, pp. 97-105.

Benoit Blank, et al., "Synthesis of Selectively Mono-N-Arylated Aliphatic Diamines via Iridium-Catalyzed Amine Alkylation", Adv. Synth. Catal., 351, 2009, pp. 2903-2911.

Young Zoo Youn, et al., "Ruthenium-catalyzed synthesis of 1-substituted-3-hydroxyperhydroazepines", Journal of Molecular Catalysis, 79. 1993, pp. 39-45.

Office Action issued Oct. 6, 2014, in Japanese Patent Application No. 2013-557049 (Translation of the Notification of Reasons for Refusal).

Ken-(chi Fujita, et al., "Oxidative Cyclization of Amino Alcohols Catalyzed by a Cp*Ir Complex. Synthesis of Indoles, 1,2,3,4-Tetrahydroquinolines, and 2,3,4,5-Tetrahydro-1-benzazepine", Organic Letters, vol. 4, No. 16, 2002, pp. 2691-2694.

K.I. Fujita, et al., "Cp*Ir Complex-Catalyzed Hydrogen Transfer Reactions Directed toward Environmentally Benign Organic Synthesis", Synlett, No, 4, 2005, pp. 560-571.

Sebastian Imm, et al., "Eine effiziente and allgemeine Synthese primarer Amine durch Ruthenium-katalysierte Aminierung sekundarer Alkohole mit Ammoniak", Angew. Chem., 122, 2010, pp. 8303-8306 (with English translation).

Dennis Pingen, et al., "Direkte Aminierung von sekundaren Alkoholen mit Ammoniak", Angew. Chem., 122, 2010, pp. 8307-8310 (with English translation).

U.S. Appl. No. 13/158,667, Wigebers, et al.

U.S. Appl. No. 13/415,412, filed Mar. 8, 2012, Schaub, et al.

U.S. Appl. No. 13/415,174, filed Mar. 8, 2012, Schaub, et al.

U.S. Appl. No. 13/415,409, filed Mar. 8, 2012, Schaub, et al.

Yoshihisa Watanabe, et al., "The Ruthenium Catalyzed N-Alkylation and N-Heterocyclization of a Aniline Using Alcohols and Aldehydes", Tetrahedron Letters, vol. 22, No. 28, 1981, pp. 2667-2670.

Sebastian Imm, et al., "Selective Ruthenium-Catalyzed Alkylation of Indoles by Using Amines", Chem. Eur. J., 16, DOI:10.1002/chem.200903261, 2010, pp. 2705-2709.

Annegret Tillack, et al., "A novel ruthenium-catalyzed amination of primary and secondary alcohols", Tetrahedron Letters 47, 2006, pp. 8881-8885.

Dirk Hollmann, et al., "A General Ruthenium-Catalyzed Synthesis of Aromatic Amines", Angnew. Chem. Int. Ed., 46, 2007, pp. 8291-8294.

Annegret Tillack, et al., "Salt-Free Synthesis of Tertiary Amines by Ruthenium-Catalyzed Amination of Alcohols", Eur. J. Org. Chem., 2008, pp. 4745-4750.

Ourida Saidi, et al., "Iridium-catalysed amine alkylation with alcohols in water", Chem. Commun., 46, 2010, pp. 1541-1543.

Ken-ichi Fujita, et al., "N-Alkylation of amines with alcohols catalyzed by a Cp*Ir complex", Tetrahedron Letters 44, 2003, pp. 2687-2690.

Yoshihisa Watanabe, et al., "Ruthenium Complex-Controlled Catalytic N-Mono- or N,N-Diakylation of Heteroaromatic amines with Alcohols", J. Org. Chem. 61, 1996, pp. 4214-4218.

Natalia Andrushko, et al., "Amination of Aliphatic Alcohols and Diols with an Iridium Pincer Catalyst", ChemCatChem, 2, 2010, pp. 640-643.

G. Jenner, et al., "Ruthenium-catalyzed Synthesis of Piperazines", Journal of Molecular Catalysis, 45, 1988, pp. 165-168.

Ainara Nova, et al., "An Experimental-Theoretical Study of the Factors that Affect the Switch between Ruthenium-Catalyzed Dehydrogenative Amide Formation versus Amine Alkylation", Organometallics, 29, DOI: 10.1021/om101015u, 2010, pp. 6548-6558.

M. Haniti S. A. Hamid, et al., "Ruthenium-Catalyzed N-Alkylation of Amines and Sulfonamides Using Borrowing Hydrogen Methodology", J. Am. Chem. Soc., 131, 2009, pp. 1766-1774.

(56) References Cited

OTHER PUBLICATIONS

Ourida Saidi, et al., "Borrowing Hydrogen in Water and Ionic Liquids: Iridium-Catalyzed Alkylation of Amines with Alcohols", Organic Process Research & Development, vol. 14, No. 4, 2010, pp. 1046-1049.
Chidambaram Gunanathan, et al., "Selective Synthesis of Primary Amines Directly from Alcohols and Ammonia", Agnew. Chem. Int. Ed., 47, 2008, pp. 8661-8664.
Ryoko Kawahara, et al., "Multialkylation of Aqueous Ammonia with Alcohols Catalyzed by Water-Soluble Cp*Ir-Ammine Complexes", J. Am. Chem. Soc., 132 DOI: 10.1021/ja107274w, 2010, 15108-15111.
Ken-ichi Fujita, et al., "Cp*Ir Complex-Catalyzed N-Heterocyclization of Primary Amines with Diols: A New Catalytic System for Environmentally Benign Synthesis of Cyclic Amines", Organic Letters, vol. 6, No. 20, 2004, pp. 3525-3528.
U.S. Appl. No. 13/516,521, filed Jun. 15, 2012, Maegerlein, et al.
U.S. Appl. No. 13/948,736, filed Jul. 23, 2013, Schelwies, et al.
U.S. Appl. No. 14/357,822, filed May 13, 2014, Strautmann, et al.

* cited by examiner

PROCESS FOR PREPARING DI-, TRI- AND POLYAMINES BY HOMOGENEOUSLY CATALYZED ALCOHOL AMINATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[This patent] *The present reissue application is a reissue application of U.S. Pat. No. 8,912,361, issued Dec. 16, 2014, which* claims the benefit of U.S. provisional patent application Ser. No. 61/450,157 filed on Mar. 8, 2011, incorporated in its entirety herein by reference.

The present invention relates to a process for preparing primary di-, tri- and polyamines by homogeneously catalyzed alcohol amination of di-, tri- and polyols and of alkanolamines having at least one primary hydroxyl group by means of ammonia with elimination of water in the presence of a complex catalyst which comprises at least one element selected from groups 8, 9 and 10 of the Periodic Table and also at least one donor ligand.

Primary amines are compounds which have at least one primary amino group (—$NH_2$). Primary diamines have two primary amino groups. Primary triamines have three primary amino groups. Primary polyamines have more than three primary amino groups.

Primary amines are valuable products having many different uses, for example solvents, stabilizers, for the synthesis of chelating agents, as starting materials for the production of synthetic resins, inhibitors, surface-active substances, intermediates in the production of fuel additives (U.S. Pat. No. 3,275,554 A, DE 2125039 A and DE 36 11 230 A), surfactants, drugs and crop protection agents, hardeners for epoxy resins, catalysts for polyurethanes, intermediates for the preparation of quaternary ammonium compounds, plasticizers, corrosion inhibitors, synthetic resins, ion exchangers, textile assistants, dyes, vulcanization accelerators and/or emulsifiers.

Primary di- and triamines are at present prepared by heterogeneously catalyzed alcohol amination of primary diols and triols by means of ammonia. WO 2008/006752 A1 describes a process for preparing amines by reacting primary or secondary alcohols with ammonia in the presence of a heterogeneous catalyst comprising zirconium dioxide and nickel. WO 03/051508 A1 relates to a process for aminating alcohols using specific heterogeneous Cu/Ni/Zr/Sn catalysts. Heterogeneous catalysts comprising nickel oxide, copper oxide, zirconium oxide and molybdenum oxide for the amination of alcohols by means of ammonia and hydrogen are known from EP 0 696 572 A1. In the abovementioned documents, the reactions are carried out at temperatures in the range from 150 to 210° C. and ammonia pressures in the range from 30 to 200 bar. However, the undesired monoamination products and cyclic amines such as piperazines, pyrrolidines and morpholines are formed as main products in the heterogeneously catalyzed processes described in the above documents. The desired primary diamines are obtained only in extremely low yields, if at all, in the above-described processes. The abovementioned documents describe, in particular, the reaction of diethylene glycol with ammonia.

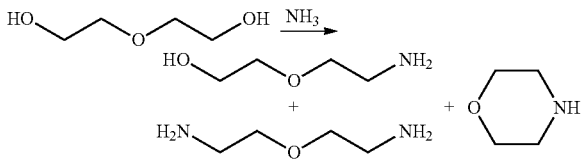

Here, monoaminodiethylene glycol and morpholine are obtained as main products. The desired doubly aminated diaminodiethylene glycol is obtained only in extremely low yields, if at all, in the amination reactions of the abovementioned documents.

The highest yield of diaminodiethylene glycol of 5% is obtained according to WO 03/051508 A1, with 22% of morpholine and 36% of monoaminodiethylene glycol being formed as by-products.

In the amination of diethanolamine by means of ammonia, piperazine is obtained as main product. Here too, the monoamination product and the desired linear diamination product diethylenetriamine are obtained only in traces.

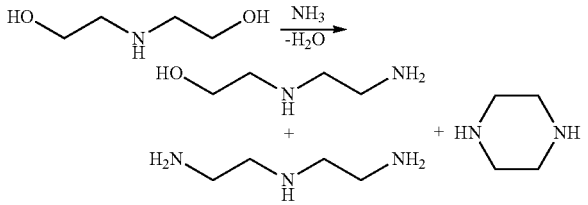

In the reaction of polyetherols, undesired secondary reactions to form the dimeric secondary amine or polymeric coupling products are observed to a substantial extent in the above-described processes for heterogeneously catalyzed amination. These by products are difficult to separate from the desired primary diamination product.

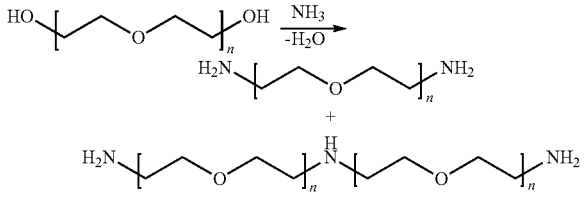

A further problem observed in the heterogeneously catalyzed amination of polyetherols, in particular polyethylene glycol and polypropylene glycol derivatives, is the decomposition of these ethers under the above-described reaction conditions, since, in particular, the high temperatures and a supporting hydrogen pressure are necessary. Under these reaction conditions, gaseous decomposition products which make specific safety precautions necessary are formed.

The homogeneously catalyzed amination of monoalcohols by means of primary and secondary amines has been known since the 1970s, with ruthenium or iridium catalysts usually being described. The homogeneously catalyzed amination proceeds at significantly lower temperatures of from 100 to 150° C. compared to heterogeneously catalyzed reactions. The reaction of monoalcohols with primary and secondary amines is described, for example, in the following publications: U.S. Pat. No. 3,708,539; Y. Watanabe, Y. Tsuji, Y. Ohsugi, Tetrahedron Lett. 1981, 22, 2667-2670; S. Bähn, S. Imm, K. Mevius, L. Neubert, A. Tillack, J. M. J. Williams, M. Beller, Chem. Eur. J. 2010, DOI: 10.1002/chem.200903144; A. Tillack, D. Hollmann, D. Michalik, M. Beller, Tetrahedron Lett. 2006, 47, 8881-8885; D. Hollmann, S. Bähn, A. Tillack, M. Beller, Angew. Chem. Int. Ed. 2007, 46, 8291-8294; A. Tillack, D. Hollmann, K. Mevius, D. Michalik, S. Bähn, M. Beller, Eur. J. Org. Chem. 2008, 4745-4750; M. H. S. A. Hamid, C. L. Allen, G. W. Lamb, A. C. Maxwell, H. C. Maytum, A. J. A. Watson, J. M. J. Williams, J. Am. Chem. Soc. 2009, 131, 1766-1774; O. Saidi, A. J. Blacker, M. M. Farah, S. P. Marsden, J. M. J. Williams, Chem. Commun. 2010, 46, 1541-1543; A. Tillack, D. Hollmann, D. Michalik, M. Beller, Tet. Lett. 2006, 47, 8881-8885; A. Del Zlotto, W. Baratta, M. Sandri, G. Verardo, P. Rigo, Eur. J. Org. Chem. 2004, 524-529; A. Fujita, Z. Li, N. Ozeki, R. Yamaguchi, Tetrahedron Lett. 2003, 44, 2687-2690; Y. Watanabe, Y. Morisaki, T. Kondo, T. Mitsudo J. Org. Chem. 1996, 61, 4214-4218, B. Blank, M. Madalska, R. Kempe, Adv. Synth. Catal. 2008, 350, 749-750, A. Martinez-Asencio, D. J. Ramon, M. Yus, Tetrahedron Lett. 2010, 51, 325-327. The greatest disadvantage of the above-described systems is that only the animation of monoalcohols by means of primary and secondary amines is possible using these processes. The reaction of alcohols with ammonia, which represents the economically most attractive animation reaction, is not described in these studies.

The animation of diols by means of secondary amines using homogeneous iridium and ruthenium catalysts to form amino alcohols and linear diamines having tertiary amino groups has been described, for example, in EP 239 934; J. A. Marsella, J. Org. Chem. 1987, 52, 467-468; U.S. Pat. No. 4,855,425; K.-T. Huh, Bull. Kor. Chem. Soc. 1990, 11, 45-49; N. Andrushko, V. Andrushko, P. Roose, K. Moonen, A. Borner, ChemCatChem, 2010, 2, 640-643 and S. Bähn, A. Tillack, S. Imm, K. Mevius, D. Michalik, D. Hollmann, L. Neubert, M. Beller, ChemSusChem 2009, 2, 551 -557. In these studies, the amination is carried out at 100-180° C.

J. A. Marsella, J. Organomet. Chem. 1991, 407, 97-105 and B. Blank, S. Michlik, R. Kempe, Adv. Synth. Catal. 2009, 351, 2903-2911; G. Jenner, G. Bitsi, J. Mol. Cat, 1988, 45, 165-168; Y. Z. Youn, D. Y. Lee, B. W. Woo, J. G. Shim, S. A. Chae, S. C. Shim, J. Mol. Cat, 1993, 79, 39-45; K. I. Fujita, R. Yamaguchi, Synlett, 2005, 4, 560-571; K. I. Fujii, R. Yamaguchi, Org. Lett. 2004, 20, 3525-3528; K. I. Fujita, K. Yamamoto, R. Yamaguchi, Org. Lett. 2002, 16, 2691-2694; A. Nova, D. Balcells, N. D. Schley, G. E. Dobereiner, R. H. Crabtree, O. Eisenstein, Organometallics DOI: 10.1021/om101015u; and M. H. S. A. Hamid, C. L. Allen, G. W. Lamb, A. C. Maxwell, H. C. Maytum, A. J. A. Watson, J. M. J. Williams, J. Am. Chem. Soc. 2009, 131, 1766-1774 and O. Saidi, A. J. Blacker, G. W. Lamb, S. P. Marsden, J. E. Taylor, J. M. J. Williams, Org. Proc. Res. Dev. 2010, 14, 1046-1049 describe the amination of diols and of alkanolamines by means of primary amines using homogeneously dissolved ruthenium- and iridium-based transition metal catalysts. However, the cyclic compounds and not the desired linear diamines are formed here. The economically attractive amination of diols by means of ammonia to form primary amines is not possible using these systems.

S. Imm, S. Bähn, L. Neubert, H. Neumann, M. Beller, Angew. Chem. 2010, 122, 8303-8306 and D. Pingen, C. Müller, D. Vogt, Angew. Chem. 2010, 122, 8307-8310 describe the animation of secondary alcohols such as cyclohexanol with ammonia which is homogeneously catalyzed by ruthenium catalysts. EP 0 320 269 A2 discloses the palladium-catalyzed amination of primary allyl monoalcohols by means of ammonia to form primary allylamines. WO 2010/018570 and C. Gunanathan, D. Milstein, Angew. Chem. Int. Ed. 2008, 47, 8661-8664 describe the amination of primary monoalcohols by means of ammonia to form primary monoamines with the help of ruthenium-phosphane complexes. The amination of primary di-, tri- and polyols is not described in these studies.

R. Kawahara, K. I. Fujita, R. Yamaguchi, J. Am. Chem. Soc. DOI: 10.1021/ja107274w describe the amination of primary monoalcohols and triols by means of ammonia using an iridium catalyst which has Cp* (1,2,3,4,5-pentamethylcyclopentadienyl) and ammonia as ligands. However, the reaction of primary monoalcohols with ammonia using the catalyst system described there gives exclusively the undesired tertiary amines. The reaction of glycerol with ammonia leads exclusively to the undesired bicyclic quinolizidine.

EP 0 234 401 A1 describes the reaction of diethylene glycol with ammonia in the presence of a ruthenium carbonyl compound. In the process described in EP 0 234 401 A1, merely the monoamination product (monoethanolamine), the secondary and tertiary amines (diethanolamine and triethanolamine) and cyclic products (N-(hydroxyethyl)piperazine and N,N'-bis(hydroxyethyl)piperazine) are formed. The desired 1,2-diethanolamine is not obtained in this process.

All the above-described processes for the reaction of diols and triols have the disadvantage that, as main products, the undesired secondary, tertiary and cyclic amines are formed. In some cases minor amounts of monoamination products such as alkanolamines are also formed. The desired primary diamines, triamines and polyamines are not accessible by this route.

It is an object of the present invention to provide a process for preparing primary di-, tri- and polyamines by alcohol amination of di-, tri- and polyols and of alkanolamines by means of ammonia with elimination of water.

The object is achieved by a process for preparing primary amines which have at least one functional group of the formula ($—CH_2—NH_2$) and at least one further primary amino group by alcohol amination of starting materials having at least one functional group of the formula ($—CH_2—OH$) and at least one further functional group (—X), where (—X) is selected from among hydroxyl groups and primary amino groups, by means of ammonia with elimination of water, wherein the reaction is carried out homogeneously catalyzed in the presence of at least one complex catalyst comprising at least one element selected from groups 8, 9 and 10 of the Periodic Table and also at least one donor ligand, in particular a phosphorus donor ligand.

It has surprisingly been found that primary di-, tri- and oligoamines can be obtained by the homogeneously catalyzed amination of diols, triols and polyols and also alkanolamines by means of ammonia with elimination of water using the complex catalysts which are used in the process of the invention and comprise at least one element selected from groups 8, 9 and 10 of the Periodic Table and also at least one donor ligand, in particular a phosphorus donor ligand. The process of the invention has the advantage that it gives primary di-, tri- and polyamines in considerably improved yields compared to the processes described in the prior art. In addition, the formation of undesired by-products such as secondary and tertiary amines and also cyclic amines is largely suppressed.

Starting Materials

In the process of the invention, starting materials having at least one functional group of the formula (—$CH_2$—OH) and at least one further functional group (—X), where (—X) is selected from among hydroxy groups and primary amino groups, are used.

In a further embodiment, starting materials in which (—X) is selected from among functional groups of the formulae (—$CH_2$—OH) and (—$CH_2$—$NH_2$) are used in the process of the invention. The starting materials then have at least one functional unit of the formula (—$CH_2$—OH) and at least one further functional unit selected from among functional units of the formulae (—$CH_2$—OH) and (—$CH_2$—$NH_2$).

Suitable starting materials are virtually all alcohols which meet the above-mentioned prerequisites. The alcohols can be straight-chain, branched or cyclic. The alcohols can also bear substituents which are inert under the reaction conditions of the alcohol amination, for example alkoxy, alkenyloxy, alkylamino, dialkylamino and halogens (F, Cl, Br, I).

Suitable starting materials which can be used in the process of the invention are, for example, diols, triols, polyols and alkanolamines, which have at least one functional group of the formula (13 $CH_2$—OH) and at least one further functional group (—X) where (—X) is selected from hydroxyl groups and primary amino groups.

In addition, diols, triols, polyols and alkanolamines which have at least one functional unit of the formula (—$CH_2$—OH) and at least one further functional unit selected from among functional units of the formula (—$CH_2$—OH) and (—$CH_2$—$NH_2$) are suitable.

As starting materials, it is possible to use all known diols which have at least one functional group of the formula (—$CH_2$—OH). Examples of diols which can be used as starting materials in the process of the invention are 1,2-ethanediol (ethylene glycol), 1,2-propanediol (1,2-propylene glycol), 1,3-propanediol (1,3-propylene glycol), 1,4-butanediol (1,4-butylene glycol), 1,2-butanediol (1,2-butylene glycol), 2,3-butanediol, 2-methyl-1,3-propanediol, 2,2-dimethyl-1,3-propanediol (neopentyl glycol), 1,5-pentanediol, 1,2-pentanediol, 1,6-hexanediol, 1,2-hexanediol, 1,7-heptanediol, 1,2-heptanediol, 1,8-octanediol, 1,2-octanediol, 1,9-nonanediol, 1,2-nonanediol, 2,4-dimethyl-2,5-hexanediol, the neopentyl glycol ester of hydroxypivalic acid, diethylene glycol, triethylene glycol, 2-butene-1,4-diol, 2-butyne-1,4-diol, polyethylene glycols, polypropylene glycols such as 1,2-polypropylene glycol and 1,3-polypropylene glycol, polytetrahydrofuran (polytetramethylene glycol), diethanolamine, 1,4-bis(2-hydroxyethyl)piperazine, diisopropanolamine, 2,5-(dimethanol)-furan, 1,4-bis(hydroxymethyl)-cyclohexane, N-butyldiethanolamine, N-methyldiethanolamine, 1,10-decanediol, 1,12-dodecanediol and C36-diol (mixture of isomers of alcohols having the empirical formula $C_{36}H_{74}O_2$).

Another name for 2,5-(dimethanol)-furan is 2,5-bis(hydroxymethyl)-furan.

Preference is given to diols having two functional groups of the formula (—$CH_2$—OH).

Particularly preferred diols are 2-ethanediol (ethylene glycol), 1,2-propanediol (1,2-propylene glycol), 1,3-propanediol (1,3-propylene glycol), 1,4-butanediol (1,4-butylene glycol), 2-methyl-1,3-propanediol, 2,2-dimethyl-1,3-propanediol (neopentyl glycol), 1,5-pentanediol, 1,6-hexanediol, 1,7-heptanediol, 1,8-octanediol, 1,9-nonanediol, diethylene glycol, triethylene glycol, polyethylene glycols, polypropylene glycols, polytetrahydrofuran, diethanolamine, 1,10-decanediol, 1,12-dodecanediol, 2,5-(dimethanol)-furan and C36-diol (mixture of isomers of alcohols having the stoichiometric formula $C_{36}H_{74}O_2$).

As diols, greatest preference is given to ethylene glycol, diethanolamine, polytetrahydrofuran, diethylene glycol, 2,5-(dimethanol)-furan and 1,4-butanediol.

As starting materials, it is possible to use all known triols which have at least one functional group of the formula (—$CH_2$—OH). Examples of triols which can be used in the process of the invention are glycerol, trimethylolpropane and triethanolamine.

Preference is given to triols which have at least two functional groups of the formula (—$CH_2$—OH).

Very particularly preferred triols are glycerol, trimethylolpropane and triethanolamine.

It is possible to use all known polyols which have at least one functional group of the formula (—$CH_2$—OH) as starting materials. Examples of polyols which can be used as starting materials in the process of the invention are 2,2-bis(hydroxymethyl)-1,3-propanediol (pentaerythritol), sugars and polymers such as glucose, mannose, fructose, ribose, deoxyribose, galactose, fucose, rhamnose, sucrose, lactose, cellobiose, maltose and amylose, cellulose, xanthan and polyvinyl alcohols.

Preference is given to polyols which have at least two functional groups of the formula (—$CH_2$—OH).

All known alkanolamines which have at least one primary hydroxyl group (—$CH_2$—OH) and at least one primary amino group (—$NH_2$) can be used as starting materials. Examples of alkanolamines which can be used as starting materials in the process of the invention are monoaminoethanol, 3-aminopropan-1-ol, 2-aminopropan-1-ol, 4-aminobutan-1-ol, 2-aminobutan-1-ol, 3-aminobutan-1-ol, 5-aminopentan-1-ol, 2-aminopentan-1-ol, 6-aminohexan-1-ol, 2-aminohexan-1-ol, 7-aminoheptan-1-ol, 2-aminoheptan-1-ol, 8-aminooctan-1-ol, 2-aminooctan-1-ol, N-(2-aminoethyl)ethanol-amine, monoaminodiethylene glycol (2-(2-aminoethoxy)ethanol), N-(2-hydroxyethyl)-1,3-propanediamine and 3-(2-hydroxyethyl)amino-1-propanol.

Preference is given to alkanolamines which have at least one primary hydroxyl group (—$CH_2$—OH) and at least one primary amino group of the formula (—$CH_2$—$NH_2$).

Very particularly preferred alkanolamines are monoaminoethanol, monoaminodiethylene glycol (2-(2-aminoethoxy)ethanol), 2-aminopropan-1-ol, 3-aminopropan-1-ol and 4-aminobutan-1-ol.

Complex Catalyst

In the process of the invention, at least one complex catalyst comprising at least one element selected from groups 8, 9 and 10 of the Periodic Table (IUPAC nomenclature) and also at least one donor ligand is used. The elements of groups 8, 9 and 10 of the Periodic Table comprise iron, cobalt, nickel, ruthenium, rhodium, palladium, osmium, iridium and platinum. Preference is given to complex catalysts which comprise at least one element selected from among ruthenium and iridium.

In one embodiment, the process of the invention is carried out homogeneously catalyzed in the presence of at least one complex catalyst of the general formula (I):

(I)

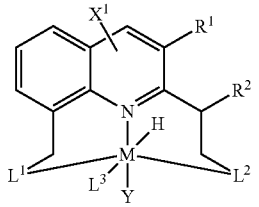

where $L^1$ and $L^2$ are each, independently of one another, phosphine ($PR^aR^b$), amine ($NR^aR^b$), sulfide, SH, sulfoxide (S(=O)R), $C_5$-$C_{10}$-heteroaryl comprising at least one heteroatom selected from among nitrogen (N), oxygen (O) and sulfur (S), arsine ($AsR^aR^b$), stibane ($SbR^aR^b$) and N-heterocyclic carbenes of the formula (II) or (III):

(II)

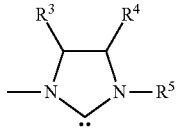

(III)

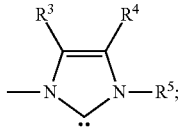

$L^3$ is a monodentate two-electron donor selected from the group consisting of carbon monoxide (CO), $PR^aR^bR^c$, $NO^+$, $AsR^aR^bR^c$, $SbR^aR^bR^c$, $SR^aR^b$, nitrile (RCN), isonitrile (RNC), nitrogen ($N_2$), phosphorus trifluoride ($PF_3$), carbon monosulfide (CS), pyridine, thiophene, tetrahydrothiophene and N-heterocyclic carbenes of the formula (II) or (III);

$R^1$ and $R^2$ are both hydrogen or together with the carbon atoms to which they are bound form a phenyl ring which together with the quinolinyl unit of the formula I forms an acridinyl unit;

R, $R^a$, $R^b$, $R^c$, $R^3$, $R^4$ and $R^5$ are each, independently of one another, unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from among N, O and S, $O_5$—$C_{1-10}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

Y is a monoanionic ligand selected from the group consisting of H, F, Cl, Br, I, OCOR, $OCOCF_3$, $OSO_2R$, $OSO_2CF_3$, CN, OH, OR and $N(R)_2$ or an uncharged molecule selected from the group consisting of $NH_3$, $N(R)_3$ and $R_2NSO_2R$;

$X^1$ represents one, two, three, four, five, six or seven substituents on one or more atoms of the acridinyl unit or one, two, three, four or five substituents on one or more atoms of the quinolinyl unit, where the radicals $X^1$ are selected independently from the group consisting of hydrogen, F, Cl, Br, I, OH, $NH_2$, $NO_2$, —NC(O)R, $C(O)NR_2$, —OC(O)R, —O(O)OR, CN and borane derivatives which can be obtained from the catalyst of the formula (I) by reaction with $NaBH_4$ and unsubstituted or at least monosubstituted alkoxy, $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S, where the substituents are selected from the group consisting of:

F, Cl, Br, OH, CN, $NH_2$ and $C_1$-$C_{10}$-alkyl;

and

M is iron, cobalt, nickel, ruthenium, rhodium, palladium, osmium, iridium or platinum.

It should be pointed out here that the complex catalyst of the formula (I) bears a positive charge when Y is an uncharged molecule selected from the group consisting of $NH_3$, $NR_3$, $R_2NSO_2R$ and M is selected from the group consisting of ruthenium, nickel, palladium, platinum and iron.

In a preferred embodiment, the process of the invention is carried out in the presence of at least one homogeneously dissolved complex catalyst of the formula (I), where the substituents have the following meanings:

$L^1$ and $L^2$, are each, independently of one another, $PR^aR^b$, $NR^aR^b$, sulfide, SH, S(=O)R, $C_5$-$C_{10}$-heteroaryl comprising at least one heteroatom selected from among N, O and S;

$L^3$ is a monodentate two-electron donor selected from the group consisting of CO, $PR^aR^bR^c$, $NO^+$, RCN, RNC, $N_2$, $PF_3$, CS, pyridine, thiophene and tetrahydrothiophene;

$R^1$ and $R^2$ are both hydrogen or together with the carbon atoms to which they are bound form a phenyl ring which together with the quinolinyl unit of the formula (I) forms an acridinyl unit;

R, $R^a$, $R^b$, $R^c$, $R^3$, $R^4$ and $R^5$ are each, independently of one another, unsubstituted $C_1$-$C_{10}$-alkyl, $C_3$ -$C_{10}$-cycloalkyl, $C_3$-$C_{10}$-heterocyclyl comprising at least one heteroatom selected from among N, O and S, $C_5$-$C_{10}$-aryl or $C_5$-$C_{10}$-heteroaryl comprising at least one heteroatom selected from among N, O and S;

Y is a monoanionic ligand selected from the group consisting of H, F, Cl, Br, OCOR, $OCOCF_3$, $OSO_2R$, $OSO_2CF_3$, CN, OH, OR and $N(R)_2$;

$X^1$ represents one, two, three, four, five, six or seven substituents on one or more atoms of the acridinyl unit or one, two, three, four or five substituents on one or more atoms of the quinolinyl unit, where $X^1$ is selected independently from the group consisting of hydrogen, F, Cl, Br, I, OH, $NH_2$, $NO_2$, —NC(O)R, $C(O)NR_2$, —OC(O)R, —C(O)OR, CN and borane derivatives which can be obtained from the catalyst of the formula (I) by reaction with $NaBH_4$ and unsubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S;

and

M is ruthenium or iridium.

In a further preferred embodiment, the process of the invention is carried out in the presence of at least one homogeneously dissolved complex catalyst where $R^1$ and $R^2$ are both hydrogen and the complex catalyst is a catalyst of the formula (IV):

(IV)

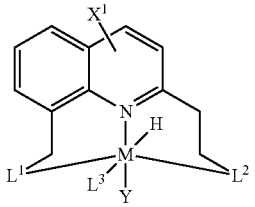

and $X^1$, $L^1$, $L^2$, $L^3$ and Y are as defined above.

In a further preferred embodiment, the process of the invention is carried out in the presence of at least one homogeneously dissolved complex catalyst where $R^1$ and $R^2$ together with the carbon atoms to which they are bound form a phenyl ring which together with the quinolinyl unit of the formula (I) forms an acridinyl unit and the complex catalyst is a catalyst of the formula (V):

(V)

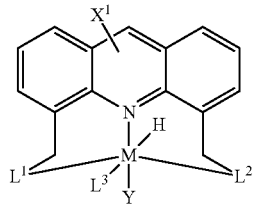

and $X^1$, $L^1$, $L^2$, $L^3$ and Y are as defined above.

Some complex catalysts (formulae (VI), (VII), (VIII), (IX), (X), (XI), (XII) and (XIII)) which can be used in the process of the invention are shown by way of example below:

(VI)

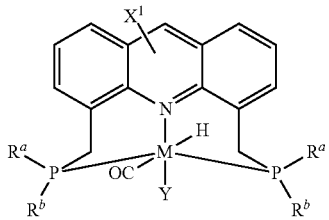

(VII)

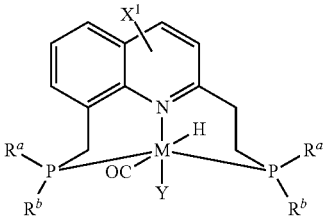

(VIII)

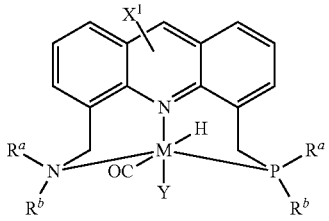

-continued (IX)

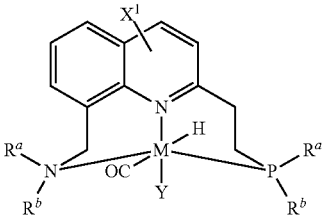

(X)

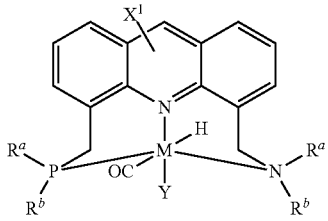

(XI)

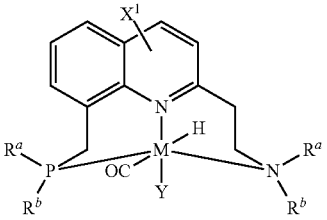

(XII)

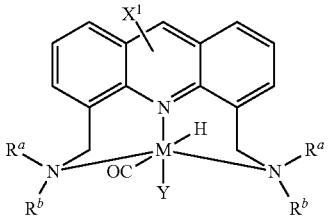

(XIII)

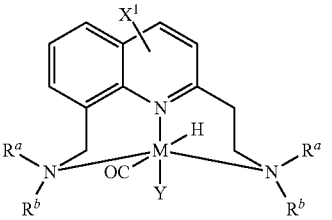

In a further preferred embodiment, the process of the invention is carried out in the presence of at least one complex catalyst selected from the group of catalysts of the formulae (VI), (VII), (VIII), (IX), (X), (XI), (XII) and (XIII), where $R^a$ and $R^b$ are each, independently of one another, unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

Y is a monoanionic ligand selected from the group consisting of H, F, Cl, Br, OCOR, $OCOCF_3$, $OSO_2R$, $OSO_2CF_3$, CN, OH, OR, $N(R)_2$;

R is unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl, $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

$X^1$ represents one, two or three substituents on one or more atoms of the acridinyl unit or one or two substituents on one or more atoms of the quinolinyl unit, where the radicals $X^1$ are selected independently from the group consisting of hydrogen, F, Cl, Br, I, OH, $NH_2$, $NO_2$, —NC(O)R, C(O)$NR_2$, —OC(O)R, —C(O)OR, CN and borane derivatives which can be obtained from the catalyst of the formula (I) by reaction with $NaBH_4$ and unsubstituted $C_1$-$C_{10}$-alkoxy, alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S;

and

M is ruthenium or iridium.

In a further preferred embodiment, the process of the invention is carried out in the presence of at least one complex catalyst selected from the group consisting of catalysts of the formulae (VI), (VII), (VIII), (IX), (X), (XI), (XII) and (XIII), where $R^a$ and $R^b$ are each, independently of one another, methyl, ethyl, isopropyl, tert-butyl, cyclohexyl, cyclopentyl, phenyl or mesityl;

Y is a monoanionic ligand selected from the group consisting of H, F, Cl, Br, $OCOCH_3$, $OCOCF_3$, $OSO_2CF_3$, CN and OH;

$X^1$ is a substituent on an atom of the acridinyl unit or a substituent on an atom of the quinolinyl unit, where $X^1$ is selected from the group consisting of hydrogen, F, Cl, Br, OH, $NH_2$, $NO_2$, —NC(O)R, C(O)$NR_2$, —OC(O)R, —C(O)OR, CN and borane derivatives which can be obtained from the catalyst of the formula (I) by reaction with $NaBH_4$ and unsubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from among N, O and S, aryl and $C_5$-$C_{10}$-heteroaryl comprising at least one heteroatom selected from among N, O and S;

M is ruthenium or iridium.

In a further preferred embodiment, the process of the invention is carried out in the presence of at least one complex catalyst from the group consisting of the catalysts of the formulae (VI), (VII), (VIII), (IX), (X), (XI), (XII) and (XIII), where $R^a$ and $R^b$ are each, independently of one another, methyl, ethyl, isopropyl, tert-butyl, cyclohexyl, cyclopentyl, phenyl or mesityl;

Y is a monoanionic ligand selected from the group consisting of H, F, Cl, Br, I, $OCOCH_3$, $OCOCF_3$, $OSO_2CF_3$, CN and OH;

$X^1$ is hydrogen;

and

M is ruthenium or iridium.

In a particularly preferred embodiment, $L^3$ is carbon monoxide (CO).

In a particularly preferred embodiment, the process of the invention is carried out in the presence of a complex catalyst of the formula (XIVa):

(XIVa)

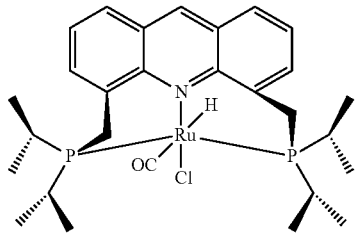

In a further particularly preferred embodiment, the process of the invention is carried out in the presence of a complex catalyst of the formula (XIVb):

(XIVb)

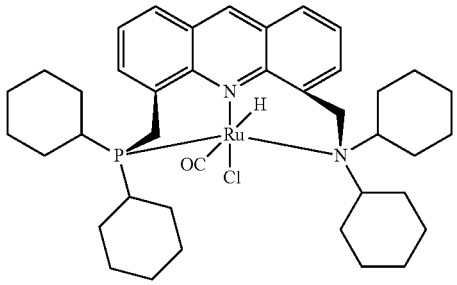

In a very particularly preferred embodiment, the process of the invention is carried out in the presence of a complex catalyst of the formula (XIVb).

In a further particularly preferred embodiment, the process of the invention is carried out in the presence of at least one homogeneously dissolved complex catalyst of the formula (XV) in which $R^1$, $R^2$, $R^3$, $L^1$, $L^2$ and $L^3$ are as defined above.

(XV)

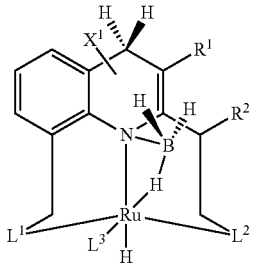

Complex catalysts of the formula (XV) can be obtained by reacting catalysts of the formula (I) with sodium borohydride ($NaBH_4$). The reaction proceeds according to the general reaction equation:

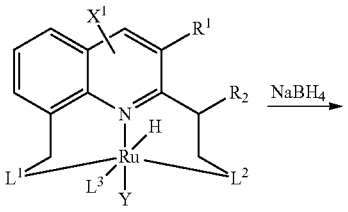

-continued

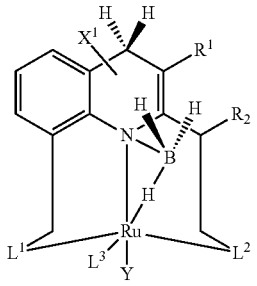

In a further particularly preferred embodiment, the process of the invention is carried out in the presence of a complex catalyst of the formula (XVIa):

(XVIa)

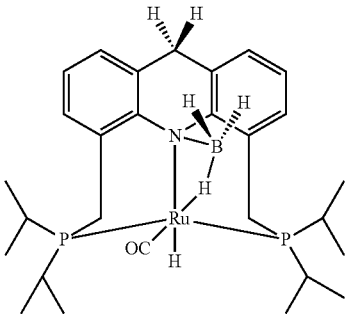

In a further particularly preferred embodiment, the process of the invention is carried out in the presence of a complex catalyst of the formula (XVIb):

(XIVb)

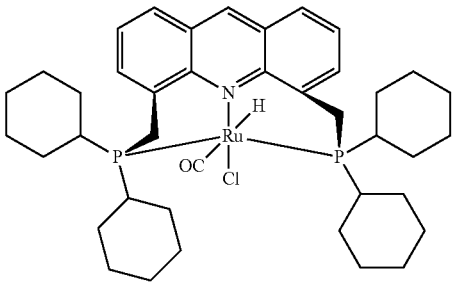

The borane derivative of the formula (XVIa) can be obtained according to the following reaction equation:

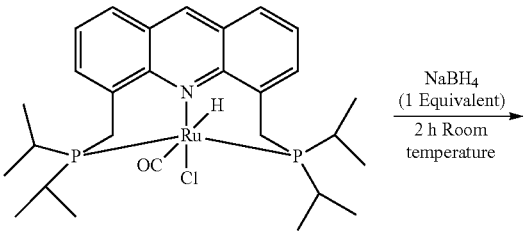

-continued

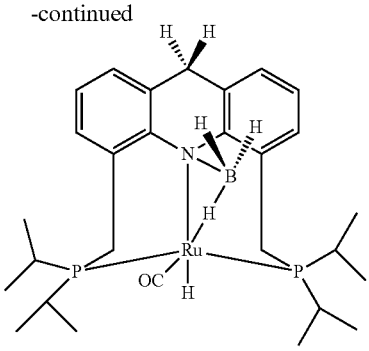

The borane derivative of the formula (XVIb) can be obtained according to the following reaction equation:

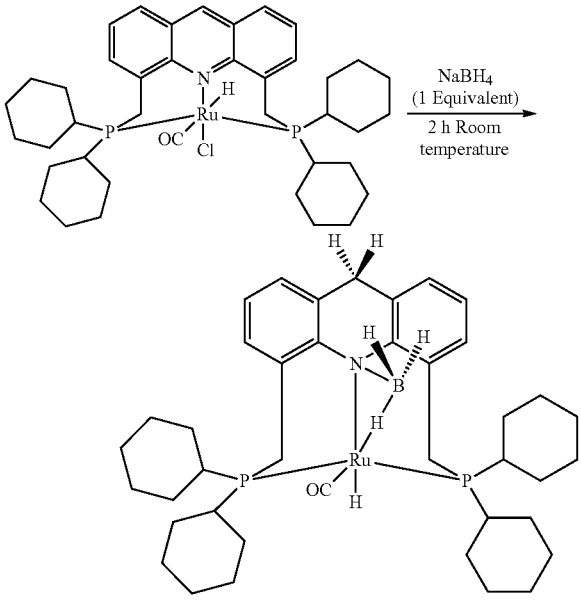

For the purposes of the present invention, the term $C_1$-$C_{10}$-alkyl refers to branched, unbranched, saturated and unsaturated groups. Preference is given to alkyl groups having from 1 to 6 carbon atoms ($C_1$-$C_6$-alkyl). Greater preference is given to alkyl groups having from 1 to 4 carbon atoms ($C_1$-$C_4$alkyl).

Examples of saturated alkyl groups are methyl, ethyl, n-propyl, isopropyl, n-butyl, isobutyl, sec-butyl, tert-butyl, amyl and hexyl.

Examples of unsaturated alkyl groups (alkenyl, alkynyl) are vinyl, allyl, butenyl, ethynyl and propynyl.

The $C_1$-$C_{10}$-alkyl group can be unsubstituted or substituted by one or more substituents selected from the group consisting of F, Cl, Br, hydroxy (OH), $C_1$-$C_{10}$-alkoxy, $C_5$-$C_{10}$-aryloxy, $C_5$-$C_{10}$-alkylaryloxy, $C_5$-$C_{10}$-heteroaryloxy comprising at least one heteroatom selected from among N, O, S, oxo, $C_3$-$C_{10}$-cycloalkyl, phenyl, $C_5$-$C_{10}$-heteroaryl comprising at least one heteroatom selected from among N, O, S, $C_5$-$C_{10}$-heterocyclyl comprising at least one heteroatom selected from among N, O, S, naphthyl, amino, $C_1$-$C_{10}$-alkylamino, $C_5$-$C_{10}$-arylamino, $C_5$-$C_{10}$-heteroarylamino comprising at least one heteroatom selected from among N, O, S, $C_1$-$C_{10}$-dialkylamino, $C_{10}$-$C_{12}$-diarylamino, $C_{10}$-$C_{20}$-alkylarylamino, $C_1$-$C_{10}$-acyl, $C_1$-$C_{10}$-acyloxy, $NO_2$, $C_1$-$C_{10}$- carboxy, carbamoyl, carboxamide, cyano, sulfonyl, sulfonylamino, sulfinyl, sulfinylamino, thiol, $C_1$-$C_{10}$-alkylthiol, $C_5$-$C_{10}$-arylthiol and $C_1$-$C_{10}$-alkylsulfonyl.

For the present purposes, the term $C_3$-$C_{10}$-cycloalkyl refers to saturated, unsaturated monocyclic and polycyclic groups. Examples of $C_3$-$C_{10}$-cycloalkyl are cyclopropyl, cyclobutyl, cyclopentyl, cyclohexyl or cycloheptyl. The cycloalkyl groups can be unsubstituted or substituted by one or more substituents as have been defined above for the $C_1$-$C_{10}$-alkyl group.

For the purposes of the present invention, $C_5$-$C_{10}$-aryl is an aromatic ring system having from 5 to 10 carbon atoms. The aromatic ring system can be monocyclic or bicyclic. Examples of aryl groups are phenyl, naphthyl such as 1-naphthyl and 2-naphthyl. The aryl group can be unsubstituted or substituted by one or more substituents as defined above under $C_1$-$C_{10}$-alkyl.

For the purposes of the present invention, $C_5$-$C_{10}$-heteroaryl is a heteroaromatic system comprising at least one heteroatom selected from the group consisting of N, O and S. The heteroaryl groups can be monocyclic or bicyclic. When the nitrogen is a ring atom, the present invention also comprises N-oxides of the nitrogen-comprising heteroaryls. Examples of heteroaryls are thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolinyl, quinolinyl, acridinyl, naphthyridinyl, quinoxalinyl, quinazolinyl, cinnolinyl, piperidinyl, carbolinyl, thiazolyl, oxazolyl, isothiazolyl, isoxazolyl. The heteroaryl groups can be unsubstituted or substituted by one or more substituents defined above under $C_1$-$C_{10}$-alkyl.

For the purposes of the present invention, the term $C_3$-$C_{10}$-heterocyclyl refers to five- to ten-membered ring systems comprising at least one heteroatom from the group consisting of N, O and S. The ring systems can be monocyclic or bicyclic. Examples of suitable heterocyclic ring systems are piperidinyl, pyrrolidinyl, pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl and tetrahydropyranyl.

Alcohol Amination

The homogeneous catalysts can be produced either directly in their active form or only under the reaction conditions from customary precursors with addition of the appropriate ligands. Customary precursors are, for example, $[Ru(p\text{-cymene})Cl_2]_2$, $[Ru(benzene)Cl_2]_n$, $[Ru(CO)_2Cl_2]_n$, $[Ru(CO)_3\ Cl_2]_2$ [Ru(COD)(allyl)], $[RuCl_3{*}H_2O]$, [Ru(acetylacetonate)$_3$], $[Ru(DMSO)_4Cl_2]$, $[Ru(PPh_3)_3(CO)(H)Cl]$, $[Ru(PPh_3)_3(CO)Cl_2]$, $[Ru(PPh_3)_3(CO)(H)_2]$, $[Ru(PPh_3)_3\ Cl_2]$, [Ru(cyclopentadienyl)$(PPh_3)_2$Cl], [Ru(cyclopentadienyl)$(CO)_2$Cl], [Ru(cyclopentadienyl)$(CO)_2$H], [Ru(cyclopentadienyl)$(CO)_2]_2$, [Ru(pentamethylcyclopentadienyl)$(CO)_2$Cl], [Ru(penta-methylcylcopentadienyl)$(CO)_2$H], [Ru(pentamethylcyclopentadienyl)$(CO)_2]_2$, [Ru(indenyl)$(CO)_2$Cl], [Ru(indenyl)$(CO)_2$H], [Ru(indenyl)$(CO)_2]_2$, ruthenocene, $[Ru(binap)Cl_2]$, $[Ru(bipyridine)_2Cl_2{*}2H_2O]$, $[Ru(COD)Cl_2]_2$, [Ru(pentamethylcyclo-pentadienyl)(COD)Cl], $[Ru_3(CO)_{12}]$, [Ru(tetraphenylhydroxycyclopentadienyl)$(CO)_2$H ], $[Ru(PMe_3)_4(H)_2]$, $[Ru(PEt_3)_4(H)_2]$, $[Ru(PnPr_3)_4(H)_2]$, $[Ru(PnBu_3)_4(H)_2]$, [Ru(Pn Octyl$_3)_4(H)_2$], $[IrCl_3{*}H_2O]$, $KIrCl_4$, $K_3IrCl_6$, $[Ir(COD)Cl]_2$, [Ir(cyclooctene)$_2$Cl]$_2$, [Ir(ethene)$_2$Cl]$_2$, [Ir(cyclopentadienyl)Cl$_2]_2$, [Ir(pentamethylcyclopentadienyl)Cl$_2]_2$, [Ir(cylopentadienyl)$(CO)_2$], [Ir(pentamethylcyclopentadienyl)$(CO)_2]$, $[Ir(PPh_3)_2(CO)(H)]$, $[Ir(PPh_3)_2(CO)(Cl)]$, $[Ir(PPh_3)_3(Cl)]$.

For the purposes of the present invention, homogeneously catalyzed means that the catalytically active part of the complex catalyst is at least partly present in solution in the liquid reaction medium. In a preferred embodiment, at least 90% of the complex catalyst used in the process is present in solution in the liquid reaction medium, more preferably at least 95%, particularly preferably more than 99%; the complex catalyst is most preferably entirely present in solution in the liquid reaction medium (100%), in each case based on the total amount in the liquid reaction medium.

The amount of the metal component of the catalyst, preferably ruthenium or iridium, is generally from 0.1 to 5000 ppm by weight, in each case based on the total liquid reaction medium.

The reaction occurs in the liquid phase, generally at a temperature of from 20 to 250° C. The process of the invention is preferably carried out at temperatures in the range from 100° C. to 200° C., particularly preferably in the range from 110 to 160° C.

The reaction can generally be carried out at a total pressure of from 0.1 to 20 MPa absolute, which can be either the autogenous pressure of the solvent at the reaction temperature or the pressure of a gas such as nitrogen, argon or hydrogen. The process of the invention is preferably carried out at a total pressure in the range from 0.5 to 10 MPa absolute, particularly preferably at a total pressure in the range from 1 to 6 MPa absolute.

The average reaction time is generally from 15 minutes to 100 hours.

The aminating agent (ammonia) can be used in stoichiometric, substoichiometric or superstoichiometric amounts based on the hydroxyl groups to be aminated.

In a preferred embodiment, ammonia is used in a from 1- to 250-fold, preferably a from 2- to 100-fold, in particular in a from 1.5- to 10-fold, molar excess per mole of hydroxyl groups to be reacted in the starting material. Higher excesses of ammonia are also possible.

The process of the invention can be carried out either in a solvent or without solvent. Suitable solvents are polar and nonpolar solvents which can be used in pure form or in mixtures. For example, it is possible to use only one nonpolar or one polar solvent in the process of the invention. It is also possible to use mixtures of two or more polar solvents or mixtures of two or more nonpolar solvents or mixtures of one or more polar solvents with one or more nonpolar solvents. The product can also be used as solvent, either in pure form or in mixtures with polar or nonpolar solvents.

Suitable nonpolar solvents are, for example, saturated and unsaturated hydrocarbons such as hexane, heptane, octane, cyclohexane, benzene, toluene, xylene and mesitylene and linear and cyclic ethers such as THF, diethyl ether, 1,4-dioxane, MTBE (tert-butyl methyl ether), diglyme and 1,2-dimethoxyethane. Preference is given to using toluene, xylene or mesitylene.

Suitable polar solvents are, for example, water, dimethylformamide, formamide, tert-amylalcohol, tert-butanol and acetonitrile. Preference is given to using water. The water can either be added before the reaction, be formed as water of reaction during the reaction or be added after the reaction in addition to the water of reaction. A further preferred solvent is tert-amylacohol. Preferred is a mixture of tert-amylalcohol and water.

To carry out the reaction in the liquid phase, ammonia, the at least one functional group of the formula (—$CH_2$—OH) and at least one further functional group of the formula (—X) having starting material, optionally together with one or more solvents, together with the complex catalyst are introduced into a reactor.

The introduction of ammonia, starting material, optionally solvent and complex catalyst can be carried out simultaneously or separately. The reaction can be carried out continuously, in the semibatch mode, in the batch mode, admixed in product as solvent or without admixing in a single pass.

It is in principle possible to use all reactors which are basically suitable for gas/liquid reactions at the given temperature and the given pressure for the process of the invention. Suitable standard reactors for gas/liquid reaction systems and for liquid/liquid reaction systems are, for example, indicated in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, chapter 3.3 "Reactors for gas-liquid reactions". Examples which may be mentioned are stirred tank reactors, tube reactors or bubble column reactors.

In the amination reaction, at least one primary hydroxyl group (—$CH_2$—OH), of the starting material is reacted with ammonia to form a primary amino group (—$CH_2$—$NH_2$), with in each case one mole of water of reaction being formed per mole of reacted hydroxyl group.

Thus, the reaction of alkanolamines having only one primary hydroxyl group (—$CH_2$—OH) forms the corresponding diamines. The reaction of monoaminoethanol thus leads to the corresponding 1,2-diaminoethane.

In the reaction of starting materials which have not only the functional group of the formula (—$CH_2$—OH) but also a further hydroxyl group (diols), both hydroxyl groups are reacted with ammonia to form the corresponding primary diamines. The reaction of 1,2-ethylene glycol thus leads to the corresponding 1,2-diaminoethane. The reaction of 2,5-(dimethanol)-furan thus leads to 2,5-bis(aminomethyl)-furan.

In the reaction of starting materials which have not only the functional group of the formula (—$CH_2$—OH) but also two further hydroxyl groups (triols), two or three hydroxyl groups are reacted with ammonia to form the corresponding primary diamines or triamines. The formation of diamines or triamines can be controlled by the amount of ammonia used and by the reaction conditions. The reaction of glycerol thus leads to the corresponding 1,2-diaminopropanol or to 1,2,3-triaminopropane.

In the reaction of starting materials which have not only the functional group of the formula (—$CH_2$—OH) but also more than three further hydroxyl groups (polyols), two, three or more hydroxyl groups are reacted with ammonia to form the corresponding primary diamines, triamines or polyamines. The formation of the corresponding primary diamines, triamines or polyamines can be controlled by the amount of ammonia used and by the reaction conditions.

The reaction output formed in the reaction generally comprises the corresponding amination products, the one or more solvents if used, the complex catalyst, possibly unreacted starting materials and ammonia and also the water of reaction formed.

Any excess ammonia present, any solvent present, the complex catalyst and the water of reaction are removed from the reaction output. The amination product obtained can be worked up further. The excess ammonia, the complex catalyst, any solvent or solvents and any unreacted starting materials can be recirculated to the amination reaction.

If the amination reaction is carried out without solvent, the homogeneous complex catalyst is dissolved in the product after the reaction. This can remain in the product or be separated off therefrom by a suitable method. Possibilities for separating off the catalyst are, for example, scrubbing with a solvent which is not miscible with the product and in which the catalyst dissolves better than in the product as a result of a suitable choice of the ligands. The catalyst concentration in the product is optionally reduced by multistage extraction. As extractant, preference is given to using a solvent which is also suitable for the target reaction, e.g. toluene, benzene, xylenes, alkanes such as hexanes, heptanes and octanes and acyclic or cyclic ethers such as diethyl ether and tetrahydrofuran, which can after concentration by evaporation be reused together with the extracted catalyst for the reaction. It is also possible to remove the catalyst by means of a suitable absorbent. The catalyst can also be separated off by adding water to the product phase if the reaction is carried out in a solvent which is immiscible with water. If the catalyst in this case dissolves preferentially in the solvent, it can be separated off with the solvent from the aqueous product phase and optionally be reused. This can be brought about by selection of suitable ligands. The resulting aqueous diamines, triamines or polyamines can be used directly as technical-grade amine solutions. It is also possible to separate the amination product from the catalyst by distillation.

If the reaction is carried out in a solvent, the latter can be miscible with the amination product and be separated off by distillation after the reaction. It is also possible to use solvents which have a miscibility gap with the amination products or the starting materials. Suitable solvents for this purpose are, for example, toluene, benzene, xylenes, alkanes such as hexanes, heptanes and octanes and acyclic or cyclic ethers such as diethyl ether, tetrahydrofuran, tert-amylalcohol and dioxane. As a result of suitable choice of the phosphine ligands, the catalyst preferentially dissolves in the solvent phase, i.e. in the phase not comprising product. The phosphine ligands can also be selected so that the catalyst dissolves in the amination product. In this case, the amination product can be separated from the catalyst by distillation.

The product may also be used as solvent. The solvent can also be miscible with the starting materials and the product under the reaction conditions and only form a second liquid phase comprising the major part of the catalyst after cooling. As solvents which display this property, mention may be made by way of example of toluene, benzene, xylenes, alkanes such as hexanes, heptanes and octanes. The catalyst can then be separated off together with the solvent and be reused. The product phase can also be admixed with water in this variant. The proportion of the catalyst comprised in the product can subsequently be separated off by means of suitable absorbents such as polyacrylic acid and salts thereof, sulfonated polystyrenes and salts thereof, activated carbons, montmorillonites, bentonites and zeolites or else be left in the product.

The amination reaction can also be carried out in a two-phase system. In the case of the two-phase reaction, suitable nonpolar solvents are, in particular, toluene, benzene, xylenes, alkanes such as hexanes, heptanes and octanes in combination with lipophilic phosphine ligands on the transition metal catalyst, as a result of which the transition metal catalyst accumulates in the nonpolar phase. In this embodiment, in which the product and the water of reaction and any unreacted starting materials form a second phase enriched with these compounds the major part of the catalyst can be separated off from the product phase by simple phase separation and be reused.

If volatile by-products or unreacted starting materials or the water formed in the reaction or added after the reaction to aid the extraction are undesirable, they can be separated off from the product without problems by distillation.

It can also be advantageous for the water formed in the reaction to be removed continuously from the reaction mixture. The water of reaction can be separated off from the reaction mixture directly by distillation or as azeotrope with addition of a suitable solvent (entrainer) and using a water separator or be removed by addition of water-withdrawing auxiliaries.

The addition of bases can have a positive effect on product formation. Suitable bases which may be mentioned here are alkali metal hydroxides, alkaline earth metal hydroxides, alkaline metal alkoxides, alkaline earth metal alkoxides, alkali metal carbonates and alkaline earth metal carbonates, of 0.01 to 100 molar equivalents, based on the metal catalyst used, can be used.

The present invention further provides for the use of a complex catalyst comprising at least one element selected from groups 8, 9 and 10 of the Periodic Table and also at least one donor ligand for the homogeneously catalyzed preparation of primary amines which have at least one functional group of the formula (—$CH_2$—$NH_2$) and at least one further primary amino group by alcohol amination of starting materials having at least one functional group of the formula (—$CH_2$—OH) and at least one further functional group (—X), where (—X) is selected from among hydroxyl groups and primary amino groups, by means of ammonia.

In a preferred embodiment, the present invention provides for the use of a homogeneously dissolved complex catalyst of the general formula (I):

(I)

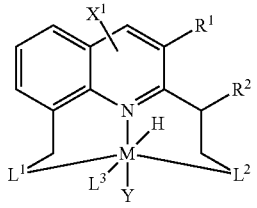

where $L^1$ and $L^2$ are each, independently of one another, $PR^aR^b$, $NR^aR^b$, sulfide, SH, S(=O)R, $C_5$-$C_{10}$-heteroaryl comprising at least one heteroatom selected from among N, O and S, $AsR^aR^b$, $SbR^aR^b$ and N-heterocyclic carbenes of the formula (II) or (III):

(II)

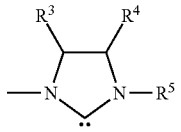

(III)

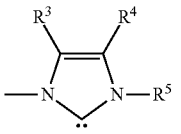

$L^3$ is a monodentate two-electron donor selected from the group consisting of CO, $PR^aR^bR^c$, $NO^+$, $AsR^aR^bR^c$, $SbR^aR^bR^c$, $SR^aR^b$, RCN, RNC, $N_2$, $PF_3$, CS, pyridine, thiophene, tetrahydrothiophene and N-heterocyclic carbenes of the formula II or III;

$R^1$ and $R^2$ are both hydrogen or together with the carbon atoms to which they are bound form a phenyl ring which together with the quinolinyl unit of the formula I forms an acridinyl unit;

R, $R^a$, $R^b$, $R^3$, $R^4$, and $R^5$ are each, independently of one another, unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

Y is a monoanionic ligand selected from the group consisting of H, F, Cl, Br, I, OCOR, $OCOCF_3$, $OSO_2R$, $OSO_2CF_3$, CN, OH, OR and $N(R)_2$ or an uncharged molecule selected from the group consisting of $NH_3$, $N(R)_3$ and $R_2NSO_2R$;

$X^1$ represents one, two, three, four, five, six or seven substituents on one or more atoms of the acridinyl unit or one, two, three, four or five substituents on one or more atoms of the quinolinyl unit, where the radicals $X^1$ are selected independently from the group consisting of hydrogen, F, Cl, Br, I, OH, $NH_2$, $NO_2$, —NC(O)R, $C(O)NR_2$, —OC(O)R, —C(O)OR, CN and borane derivatives which can be obtained from the catalyst of the formula I by reaction with $NaBH_4$ and unsubstituted or at least monosubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

and

M is iron, cobalt, nickel, ruthenium, rhodium, palladium, osmium, iridium or platinum, for the homogeneously catalyzed preparation of primary amines which have at least one functional group of the formula (—$CH_2$—$NH_2$) and at least one further primary amino group by alcohol amination of starting materials having at least one functional group of the formula (—$CH_2$—OH) and at least one further functional group (—X), where (—X) is selected from among hydroxyl groups and primary amino groups, by means of ammonia, where the definitions and preferences described above for the process of the invention apply to the catalyst of the general formula (I).

In a further preferred embodiment, the present invention relates to the use of a homogeneously dissolved complex catalyst of the general formula (XV):

(XV)

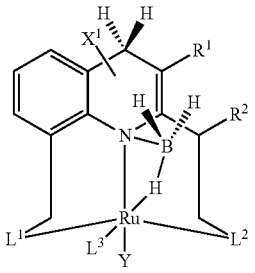

where $L^1$ and $L^2$ are each, independently of one another, $PR^aR^b$, $NR^aR^b$, sulfide, SH, S(=O)R, $C_5$-$C_{10}$-heteroaryl comprising at least one heteroatom selected from among N, O and S, $AsR^aR^b$, $SbR^aR^b$ or N-heterocyclic carbenes of the formula (II) or (III):

(II)

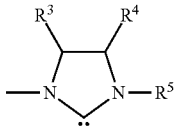

(III)

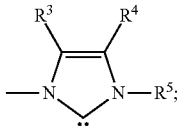

$L^3$ is a monodentate two-electron donor selected from the group consisting of CO, $PR^aR^bR^c$, $NO^+$, $AsR^aR^bR^c$, $SbR^aR^bR^c$, $SR^aR^b$, RCN, RNC, $N_2$, $PF_3$, CS, pyridine, thiophene, tetrahydrothiophene and N-heterocyclic carbenes of the formula (II) or (III);

$R^1$ and $R^2$ are both hydrogen or together with the carbon atoms to which they are bound form a phenyl ring which together with the quinolinyl unit of the formula (I) forms an acridinyl unit;

R, $R^a$, $R^b$, $R^c$, $R^3$, $R^4$ and $R^5$ are each, independently of one another, unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl or $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

Y is a monoanionic ligand selected from the group consisting of H, F, Cl, Br, I, OCOR, $OCOCF_3$, $OSO_2R$, $OSO_2CF_3$, CN, OH, OR and $N(R)_2$ or uncharged molecules selected from the group consisting of $NH_3$, $N(R)_3$ and $R_2NSO_2R$;

$X^1$ represents one, two, three, four, five, six or seven substituents on one or more atoms of the acridinyl unit or one, two, three, four or five substituents on one or more atoms of the quinolinyl unit, where the radicals $X^1$ are selected independently from the group consisting of hydrogen, F, Cl, Br, I, OH, $NH_2$, $NO_2$, —NC(O)R, $C(O)NR_2$, —OC(O)R, —C(O)OR, CN and borane derivatives which can be obtained from the catalyst of the formula I by reaction with $NaBH_4$ and unsubstituted or at least monosubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from among N, O and S, $C_5$-$C_{10}$-aryl and $C_5$-$C_{10}$-heteroaryl comprising at least one heteroatom selected from among N, O and S, where the substituents are selected from the group consisting of: F, Cl, Br, OH, CN, $NH_2$ and $C_1$-$C_{10}$-alkyl;

and

M is iron, cobalt, nickel, ruthenium, rhodium, palladium, osmium, iridium or platinum, for the homogeneously catalyzed preparation of primary amines which have at least one functional group of the formula (—$CH_2$—$NH_2$) and at least one further primary amino group by alcohol amination of starting materials having at least one functional group of the formula (—$CH_2$—OH) and at least one further functional group (—X), where (—X) is selected from among hydroxyl groups and primary amino groups, by means of ammonia, where the definitions and preferences described above for the process of the invention apply to the catalyst of the general formula I.

The invention is illustrated by the following examples without being restricted thereto.

EXAMPLES

General Method for the Catalytic Amination of Alcohols by Means of Ammonia According to the Invention Catalyst complex XIVb (for preparation, see below, weighed out under an inert atmosphere), solvent (such an amount that the total solvent volume is 50 ml) and the alcohol to be reacted were placed under an argon atmosphere in a 160 ml Parr autoclave (stainless steel V4A) having a magnetically coupled inclined blade stirrer (stirring speed: 200-500 revolutions/minute). The indicated amount of ammonia was introduced at room temperature either in precondensed form or directly from the pressurized $NH_3$ gas bottle. If hydrogen was used, this was effected by iterative differential pressure metering. The steel autoclave was electrically heated to the temperature indicated and heated for the time indicated while stirring (500 revolutions/minute) (internal temperature measurement). After cooling to room temperature, venting the autoclave and outgassing the ammonia at atmospheric pressure, the reaction mixture was analyzed by GC (30m RTX5 amine 0.32 mm 1.5 μm). Purification of the particular products can, for example, be carried out by distillation. The results for the amination of 1,4-butanediol (table 1a, 1b), diethylene glycol (table 2) and monoethylene glycol (table 3), 2,5-furandimethanol (table 4), alkyldiols (table 5), 1,4-bis(hydroxymethyl)-cyclohexane (table 6) and aminoalcohols (table 7) are given below.

Synthesis of the Catalyst Complex XIVb

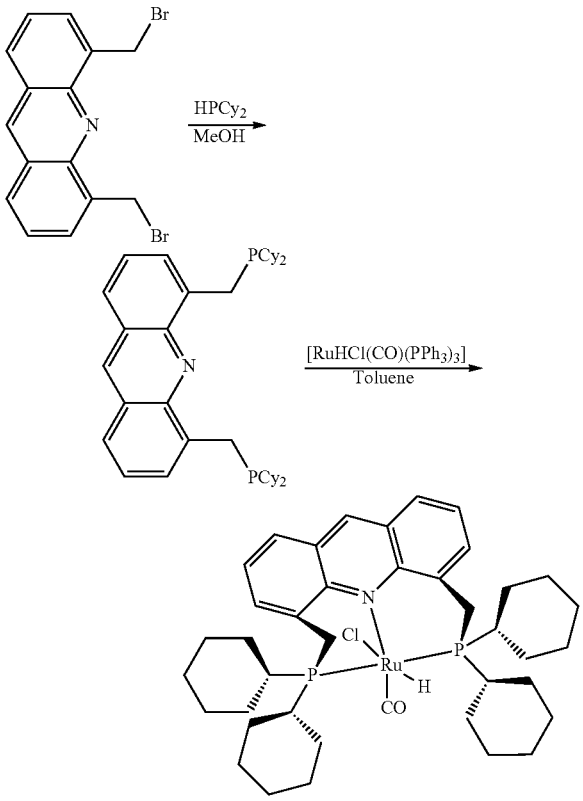

XIVb a) Synthesis of 4,5-bis(dicyclohexylphosphinomethyl)acridine

A solution of 4,5-bis(bromomethyl)acridine[1] (5.2 g, 14.2 mmol) and dicyclohexylphosphine (8.18 g, 36.8 mmol) in 65 ml of anhydrous, degassed methanol was heated at 50° C. under an inert argon atmosphere for 66 hours. After cooling to room temperature, triethylamine (5.72 g, 56.7 mmol) was added and the mixture was stirred for 1 hour. Evaporation of the solvent gave a whitish yellow solid in a red oil. Extraction by means of 3×40 ml of MTBE and concentration of the filtrate gave a reddish brown oil ($^1$H NMR: mixture of product & $HPCy_2$). Taking up in a little warm MTBE followed by addition of ice-cooled methanol resulted in precipitation of a yellow, microcrystalline solid. Oscillation and drying under reduced pressure gave air sensitive 4,5-bis(dicyclohexylphosphinomethyl)acridine (2.74 g, 33%) as a yellow powder. $^1$H NMR (360.63 MHz, d8-toluene): δ [ppm]=8.07 (s, 1H, H9), 7.91 (d, J=8.3 Hz, 2H, Ar—H), 7.42 (d, J=8.3 Hz, 2H, Ar—H), 7.21 (dd, J=8.3 Hz, J=7.2 Hz, 2H, Ar—H), 3.89 (bs, 4H, —$CH_2$—P), 1.96-1.85 (m, 8H, Cy-H), 1.77-1.54 (m, 20H, Cy-H), 1.26-1.07 (m, 16H, Cy-H). $^{31}P\{^1H\}$ NMR (145.98 MHz, d8-toluene): δ [ppm]= 2.49 (s, —$CH_2$—$P(Cy)_2$).

b) Synthesis of the Catalyst Complex XIVb 4,5-bis(dicyclohexylphosphinomethyl)acridine (1855 mg, 3.1 mmol) and $[RuHCl(CO)(PPh_3)_3]$[2] (2678 mg, 2.81 mmol) were heated at 70° C. in 80 ml of degassed toluene for 2 hours. The resulting dark brown solution was evaporated to dryness, the residue was slurried in 3×20 ml of hexane and isolated by filtration. Drying under reduced pressure gave the catalyst complex XIVb (1603 mg, 75%) as an orange-brown powder. $^1$H NMR (360.63 MHz, d8-toluene): δ [ppm]=8.06 (s, 1H, H9), 7.43 (d, J=7.6 Hz, 2H, Ar—H), 7.33 (d, J=6.5 Hz, 2H, Ar—H), 7.06-7.02 (m, 2H, Ar—H), 5.02 (d, J=11.9 Hz, 2H, —CHH—$PCy_2$), 3.54 (d, J=12.2 Hz, 2H, —CHH—$PCy_2$), 2.87 (bs, 2H, —$P(C_aH(CH_2)_5)_2$), 2.54 (bs, 2H, —$P(C_bH(CH_2)_5)_2$), 2.18 (bs, 2H, Cy-H), 1.88-1.85 (m, 8H, Cy-H), 1.65 (bs, 6H, Cy-H), 1.42-1.35 (m, 14H, Cy-H), 1.17-0.82 (m, 12H, Cy-H), −16.29 (t, J=19.1 Hz, 1H, Ru—H). $^{31}P\{^1H\}$ NMR (145.98 MHz, d8-toluene): δ [ppm]=60.89 (s, —$CH_2$—$P(Cy)_2$).

[1] J. Chiron, J. P. Galy, Synlett, 2003, 15.

[2] Literature instructions: Inorganic Syntheses 1974, 15, 48. See also: T. Joseph, S. S. Deshpande, S. B. Halligudi, A. Vinu, S. Ernst, M. Hartmann, J. Mol. Cat. (A) 2003, 206, 13-21.

TABLE 1a

Reaction of 1,4-butanediol

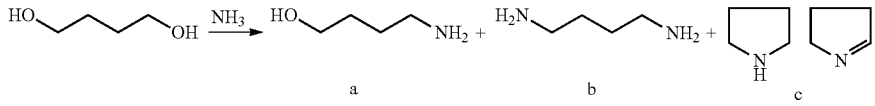

| No[a)] | Solvent | T [° C.] | Time [h] | $NH_3$ [eq][d)] | Reaction pressure [bar] | Further condition | Conversion[b)] | Selectivity[c)] a | b | c |
|---|---|---|---|---|---|---|---|---|---|---|
| 1 | Toluene | 155 | 12 | 6 | 44 | 0.2 mol % of KOtBu | 43.3 | 60.1 | 12.1 | 18.7 |
| 2 | Toluene | 155 | 12 | 6 | 41 | 1.0 mol % of KOtBu | 37.0 | 61.9 | 11.4 | 18.7 |
| 3 | Toluene | 155 | 24 | 9 | 51 | | 87.0 | 50.3 | 14.8 | 30.8 |
| 4 | Toluene | 155 | 60 | 6 | 57 | 5 bar of $H_2$ injected cold | 58.7 | 62.2 | 18.8 | 18.3 |
| 5 | p-Xylene | 180 | 12 | 6 | 51 | — | 100.0 | 0.6 | 51.0 | 43.6 |
| 6 | p-Xylene | 180 | 12 | 6 | 47 | 5.0 mol % of water | 99.9 | 0.7 | 46.7 | 48.6 |

[a)]conditions unless indicated otherwise: 50 ml of solvent, batch size 25 mmol of 1,4-butanediol, 0.1 mol % of catalyst complex XIVb (per alcohol group),
[b)]evaluation by GC (% by area),
[c)]product selectivity determined by GC,
[d)]molar equivalents of $NH_3$ per OH function on the substrate TABLE 1b Reaction of 1,4-butanediol

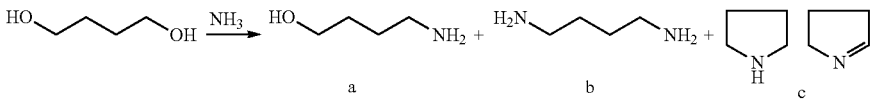

| No[a)] | Solvent (waterfree) | T [° C.] | Time [h] | $NH_3$ [eq][d)] | Reaction-pressure [bar] | Further conditions[e)] | Conversion[b)] [%] | Selectivity[c)] a [%] | b [%] | c [%] |
|---|---|---|---|---|---|---|---|---|---|---|
| 1 | Toluol | 155 | 12 | 6 | 46.1 | 0.2 mol % KOH (aq. 20%) | 59.25 | 59.14 | 16.42 | 19.89 |
| 2 | Toluol | 155 | 15 | 6 | 42.0 | — | 96.06 | 17.90 | 14.20 | 62.10 |
| 3 | Toluol | 155 | 24 | 6 | 40.2 | — | 98.92 | 8.60 | 20.38 | 64.91 |
| 4 | Toluol | 180 | 2 | 6 | 52.7 | — | 91.52 | 36.35 | 25.76 | 35.39 |
| 5 | Toluol | 180 | 9 | 6 | 48.0 | — | 100.00 | 0.12 | 19.90 | 73.67 |
| 6 | Toluol | 180 | 12 | 6 | 69.7 | 5 bar H2 | 94.19 | 30.09 | 37.23 | 31.62 |
| 7 | Toluol | 180 | 12 | 6 | 81.9 | 10 bar H2 | 89.85 | 36.24 | 35.41 | 27.66 |
| 8 | Dioxane | 180 | 12 | 6 | 44.3 | — | 100.00 | 1.15 | 23.79 | 71.23 |
| 9 | THF | 180 | 12 | 6 | 46.9 | — | 100.00 | 0.00 | 17.03 | 77.33 |
| 10 | THF | 180 | 12 | 9 | 62.3 | — | 100.00 | 0.00 | 20.16 | 71.30 |
| 11 | THF | 180 | 12 | 6 | 71.7 | 5 bar H2 | 99.87 | 2.41 | 26.28 | 67.55 |

[a)]condition unless indicated otherwise: 50 ml solvent, batch size 25 mmol 1,4-butanediol;

[b)]evaluation by GC (% by area),

[c)]product selectivity determined by GC;

[d)]molar equivalents $NH_3$ per OH function on the substrate;

[e)]mol % based on the OH functions on the substrate

TABLE 2a

Reaction of diethylene glycol

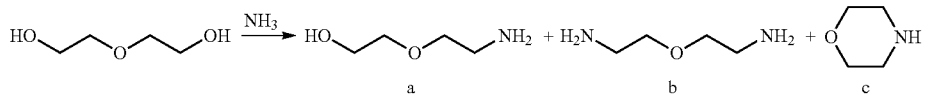

| No[a)] | Solvent | T [° C.] | Time [h] | $NH_3$ [eq][d)] | Reaction pressure [bar] | Further condition | Conversion[b)] | Selectivity[c)] a | b | c |
|---|---|---|---|---|---|---|---|---|---|---|
| 1 | Toluene | 155 | 12 | 6 | 40 | | 79.0 | 51.4 | 23.8 | 12.9 |
| 2 | Toluene | 155 | 12 | 6 | 43 | | 82.4 | 55.3 | 20.1 | 10.9 |
| 3 | Toluene | 155 | 12 | 6 | 42 | 0.2 mol % of KOtBu | 69.8 | 41.8 | 31.9 | 14.3 |
| 4 | Toluene | 155 | 12 | 6 | 43 | 1.0 mol % of KOtBu | 60.4 | 44.7 | 25.8 | 14.8 |
| 5 | Toluene | 155 | 60 | 6 | 58 | 5 bar of H2 | 66.5 | 57.1 | 31.0 | 9.9 |
| 6 | p-Xylene | 155 | 12 | 6 | 38 | 1.0 mol % of water | 77.5 | 52.9 | 21.6 | 16.9 |
| 7 | p-Xylene | 155 | 12 | 6 | 41 | 5 mol % of water | 84.0 | 49.0 | 21.1 | 12.8 |
| 8 | p-Xylene | 155 | 15 | 6 | 46 | | 77.5 | 49.1 | 23.7 | 13.1 |
| 9 | p-Xylene | 155 | 24 | 6 | 44 | | 96.3 | 17.0 | 48.6 | 19.9 |
| 10 | p-Xylene | 155 | 24 | 6 | 53 | 1.0 mol % of water | 84.6 | 51.8 | 20.8 | 12.9 |
| 11 | p-Xylene | 180 | 12 | 6 | 50 | | 100.0 | 0.4 | 46.1 | 27.9 |
| 12 | p-Xylene | 180 | 12 | 6 | 50 | 5 mol % of H2O | 100.0 | 0.4 | 48.2 | 27.4 |

[a)]conditions unless indicated otherwise: 50 ml of solvent, batch size 25 mmol of diethylene glycol, 0.1 mol % of catalyst complex XIVb (per alcohol group);

[b)]evaluation by GC (% by area);

[c)]product selectivity determined by GC;

[d)]molar equivalents of $NH_3$ per OH function on the substrate;

[f)]batch size 35 mmol of diethylene glycol in 70 ml of solvent

TABLE 2b

Reaction of diethylene glycol

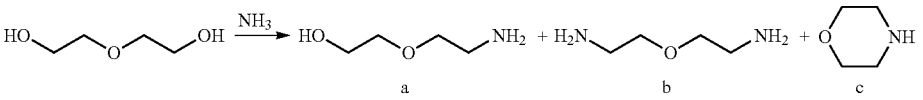

| No.[a] | Solvent (waterfree) | Catalyst | T [° C.] | Time [h] | $NH_3$ [eq][d] | Reaction pressure (bar) | Further conditions[e] | Conversion[b] [%] | Selectivity[c] a [%] | b [%] | c [%] |
|---|---|---|---|---|---|---|---|---|---|---|---|
| 1 | Toluol | XIVb | 155 | 12 | 2.0 | 12.3 | | 83.52 | 37.60 | 13.93 | 25.58 |
| 2 | Toluol | XIVb | 155 | 12 | 6 | 40.9 | 0.2 mol % KOH (aq. 20%) | 73.94 | 39.35 | 37.29 | 15.28 |
| 3 | Toluol | XIVb | 155 | 24 | 6 | 43.6 | | 97.31 | 18.10 | 36.58 | 21.66 |
| 4 | Toluol | XIVb | 155 | 15 | 6 | 45.7 | 0.05 mol % XIVb | 95.97 | 17.66 | 40.46 | 26.67 |
| 5 | Toluol | XIVb | 155 | 12 | 6 | 65.5 | 5 bar H2 | 61.84 | 69.16 | 18.61 | 8.01 |
| 6 | Toluol | XIVb | 155 | 12 | 6 | 36.0 | 25 g t-Butanol, 25 ml Toluol | 86.90 | 44.98 | 26.76 | 15.52 |
| 7 | Toluol | XIVb | 165 | 12 | 6 | 45.1 | | 98.22 | 12.52 | 40.92 | 21.86 |
| 8 | Toluol | XIVb | 170 | 12 | 6 | 45.7 | | 99.81 | 4.39 | 43.66 | 26.02 |
| 9 | Toluol | XIVb | 180 | 2 | 6 | 47.2 | 0.2 mol % XIVb | 95.81 | 19.45 | 41.17 | 19.87 |
| 10 | Toluol | XIVb | 180 | 9 | 6 | 45.5 | | 100.00 | 0.75 | 39.21 | 29.46 |
| 11 | Toluol | XIVb | 180 | 12 | 6 | 37.7 | | 100.00 | 0.00 | 32.75 | 38.67 |
| 12 | Toluol | XIVb | 180 | 12 | 6 | 69.7 | 5 bar H2 | 96.05 | 20.68 | 54.70 | 16.64 |
| 13 | Toluol | XIVb | 180 | 12 | 6 | 75.6 | 10 bar H2 | 86.11 | 35.73 | 47.22 | 13.77 |
| 14 | Dioxane | XIVb | 155 | 12 | 6 | 38.0 | | 68.17 | 65.02 | 20.29 | 9.21 |
| 15 | Dioxane | XIVb | 180 | 12 | 6 | 34.1 | | 99.66 | 4.65 | 40.23 | 34.65 |
| 16 | THF | XIVb | 155 | 12 | 6 | 41.0 | | 70.97 | 54.46 | 19.41 | 11.95 |
| 17 | THF | XIVb | 155 | 12 | 9 | 51.9 | | 81.65 | 53.75 | 23.60 | 13.51 |
| 18 | THF | XIVb | 180 | 12 | 6 | 49.1 | | 100.00 | 0.00 | 42.48 | 41.98 |
| 19 | Toluol | XIVa | 155 | 12 | 6 | 40.7 | | 68.02 | 69.62 | 9.60 | 9.52 |
| 20 | Toluol | XIVa | 155 | 24 | 6 | 42.1 | | 77.16 | 43.54 | 20.09 | 15.10 |

[a]conditions unless indicated otherwise: 50 ml of solvent, batch size 25 mmol of diethylene glycol, 0.1 mol % of catalyst complex XIVa or XIVb (per alcohol group);

[b]evaluation by GC (% by area);

[c]product selectivity determined by GC;

[d]molar equivalents of $NH_3$ per OH function on the substrate;

[e]mol % based on the OH function on the substrate

TABLE 3a

Reaction of MEG (monoethylene glycol)

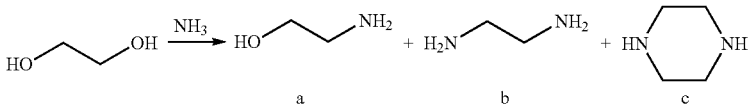

| No.[a] | Solvent | T [° C.] | Time [h] | $NH_3$ [eq][d] | Reaction pressure (bar) | Further conditions | Conversion[b] | Selectivity[c] a | b | c |
|---|---|---|---|---|---|---|---|---|---|---|
| 1 | Toluene | 155 | 12 | 6 | 42 | 0.2 mol % of KOtBu | 62.9 | 47.5 | 25.0 | 0.5 |
| 2 | Toluene | 155 | 12 | 6 | 41 | 1 mol % of KOtBu | 75.9 | 39.9 | 26.8 | 0.3 |
| 3 | Toluene | 155 | 12 | 6 | 44 | | 19.3 | 48.3 | 21.8 | 0.6 |
| 4 | Toluene | 155 | 12 | 6 | 42 | 17 eq. of water | 21.6 | 55.6 | 36.4 | 0.0 |

[a]conditions unless indicated otherwise: 50 ml of solvent, batch size 25 mmol of monoethylene glycol, 0.1 mol % of catalyst complex XIVb (per alcohol group),

[b]evaluation by GC (% by area),

[c]product selectivity determined by GC,

[d]molar equivalents of $NH_3$ per OH function on the substrate

TABLE 3b

Reaction of MEG (monoethylene glycol)

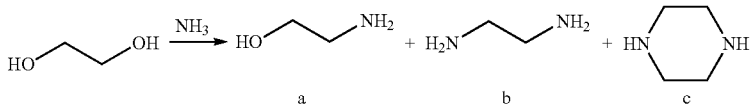

| No.[a] | Solvent (waterfree) | catalyst | T [° C.] | Time [h] | $NH_3$ [eq][d] | Reaction pressure (bar) | Further conditions') | Conversion[b] [%] | Selectivity[c] a [%] | b [%] | c [%] |
|---|---|---|---|---|---|---|---|---|---|---|---|
| 1 | Toluol | XIVb | 155 | 12 | 6 | 39.8 | 0.2 mol % KOH (aq, 20%) | 59.98 | 41.02 | 22.73 | 12.92 |
| 2 | Toluol | XIVb | 180 | 12 | 6 | 46.8 | — | 94.72 | 11.00 | 19.72 | 44.48 |
| 3 | Toluol | XIVb | 180 | 12 | 6 | 47.4 | 1 mol % KOtBu | 100.00 | 0.66 | 21.17 | 49.04 |
| 4 | Toluol | XIVb | 180 | 12 | 6 | 66.1 | 5 bar H2 | 85.23 | 15.49 | 26.30 | 45.17 |
| 5 | p-Xylol | XIVb | 155 | 24 | 6 | 45.8 | — | 45.78 | 43.94 | 18.28 | 0.22 |
| 6 | THE | XIVb | 155 | 12 | 6 | 41.7 | 2 mol % KOtBu | 56.85 | 47.52 | 18.66 | 1.98 |
| 7 | THF | XIVb | 180 | 12 | 6 | 47.2 | — | 88.49 | 10.02 | 22.50 | 46.63 |
| 8 | Toluol | XIVa | 180 | 24 | 6 | 28.0 | — | 100.00 | 6.39 | 11.51 | 60.53 |
| 9 | Toluol | XIVa | 155 | 12 | 6 | 40.8 | 1 mol % KOtBu | 50.47 | 52.84 | 19.81 | 4.31 |

[a]conditions unless indicated otherwise: 50 ml of solvent, batch size 25 mmol of monoethylene glycol, 0.1 mol % of catalyst complex XIVa or XIVb (per alcohol group);

[b]evaluation by GC (% by area);

[c]product selectivity determined by GC;

[d]molar equivalents of $NH_3$ per OH function on the substrate;

[e]mol % based on the OH functions on the substrate

TABLE 4

Reaction of 2,5-furandimethanol

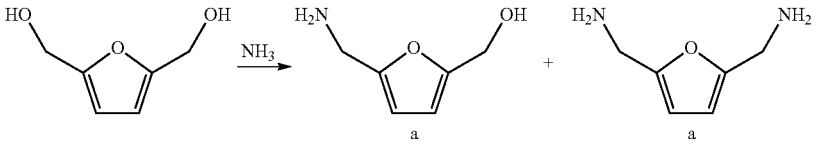

| No.[a] | Solvent (waterfree) | Catalyst | T [° C.] | Time [h] | $NH_3$ [eq][d] | Reaction Pressure (bar) | Conversion[b] [%] | Selectivity[c] a [%] | b [%] |
|---|---|---|---|---|---|---|---|---|---|
| 1 | THF | XIVb | 140 | 21 | 6 | 35.2 | 100.00 | 0.40 | 96.36 |
| 2 | THF | XIVb | 150 | 6 | 6 | 38.8 | 100.00 | 7.14 | 87.75 |
| 3 | THF | XIVb | 150 | 12 | 6 | 40.4 | 100.00 | 0.27 | 84.44 |
| 4 | THF | XIVb | 150 | 18 | 6 | 37.1 | 100.00 | 0.31 | 94.15 |
| 5 | t-amylalcohol | XIVb | 140 | 9 | 6 | 31.4 | 99.59 | 9.55 | 84.97 |
| 6 | t-amylalcohol | XIVb | 150 | 5 | 6 | 37.1 | 100.00 | 2.70 | 90.10 |
| 7 | t-amylalcohol | XIVb | 150 | 18 | 6 | 37.9 | 100.00 | 0.00 | 95.60 |

[a]conditions unless indicated otherwise: 50 ml of solvent, batch 25 mmol of 2,5-furandimethanol, 0.1 mol % of catalyst complex XIVb (per alcohol group);

[b]evaluation by GC (% by area);

[c]product selectivity determined by GC;

[d]molar equivalents of $NH_3$ per OH function on the substrate

TABLE 5

Reaction of alkyldiols

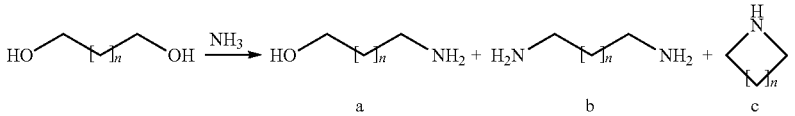

| No.[a] | Alcohol | Solvent (waterfree) | catalyst | T [° C.] | Time [h] | $NH_3$ [eq][d] | Reaction Pressure (bar) | Conversion[b] [%] | Selectivity[c] a [%] | b [%] | c [%] |
|---|---|---|---|---|---|---|---|---|---|---|---|
| 1 | 1,3-propanediol | Toluol | XIVb | 135 | 12 | 6 | 41.1 | 99.73 | 8.95 | 35.79 | |
| 2 | 1,5-pentanediol | Toluol | XIVb | 180 | 12 | 6 | 44.1 | 80.51 | 58.26 | 19.24 | 15.13 |
| 3 | 1,6-hexanediol | Toluol | XIVb | 155 | 12 | 6 | 34.0 | 100.00 | 1.14 | 91.38 | 0.51 |
| 4[e] | 1,9-nonanediol | THF | XIVb | 150 | 24 | 6 | 15.0 | 97.70 | 10.60 | 74.60 | |
| 5 | 1,10-decanediol | Toluol | XIVb | 155 | 12 | 6 | 44.3 | 95.19 | 1.36 | 93.25 | |
| 6 | $C_{36}$-diol | THF | XIVb | 155 | 12 | 6 | 38.2 | Amine number (AZ)[f]: 197<br>AZ (primary amines): 196<br>AZ (secondary Amines) < 1<br>AZ (tertiary amines): 1 | | | |

[a]conditions unless indicated otherwise: 50 ml of solvent, batch size 25 mmol of alkyldiol, 0.1 mol % of catalyst complex XIVb (per alcohol group);
[b]evaluation by GC (% by area);
[c]product selectivity determined by GC;
[d]molar equivalents of $NH_3$ per OH function on the substrate;
[e]batch size: 50 mmol 1,9-nonanediol in a 100 ml autoclave;
[f]definition of amine number (AZ), see Thieme Rompp Chemielexikon

TABLE 6

Reaction of 1,4-bis(aminomethyl)cyclohexane

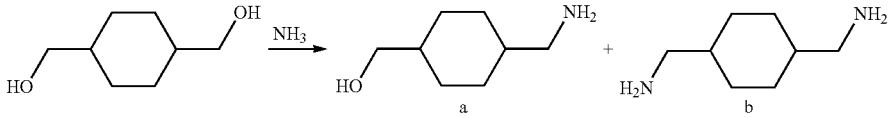

| No.[a] | Alcohol | Solvent (waterfree) | Catalyst | T [° C.] | Time [h] | $NH_3$ [eq][d] | Reaction-pressure [bar] | Conversion[b] [%] | Selectivity[c] a [%] | b [%] |
|---|---|---|---|---|---|---|---|---|---|---|
| 1 | 1,4-bis(hydroxymethyl)cyclohexane | THF | XIVb | 155 | 12 | 6 | 45.5 | 100.00 | 0.63 | 94.35 |

[a]50 ml solvent, 25 mmol 1,4-(bishydroxymethyl)cyclohexane, 0.1 mol %catalyst complex XIVb (per alcohol group);
[b]evaluation by GC (% by area);
[c]product selectivity determined by GC;
[d]molar equivalents $NH_3$ per OH function on the substrate

TABLE 7

Reaction of α,ω-alkanol amines

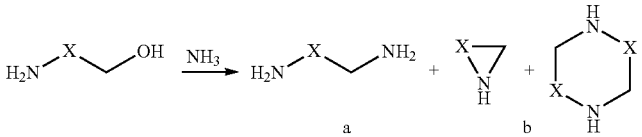

| No.[a] | Alcohol | Solvent (waterfree) | catalyst | T [° C.] | Time [h] | $NH_3$ [eq][d] | Reaction pressure [bar] | Conversion[b] [%] | Selectivity[c] a [%] | b [%] |
|---|---|---|---|---|---|---|---|---|---|---|
| 1 | 3-aminopropane-1-ol | Toluol | XIVb | 135 | 12 | 6 | 35.2 | 45.54 | 46.98 | |
| 2[e] | 4-aminobutane-1-ol | THF | XIVb | 180 | 12 | 6 | 24.8 | 77.21 | 9.48 | 85.24 |
| 3 | 2-(2-aminoethoxy)ethanol | Toluol | XIVb | 155 | 15 | 6 | 41.7 | 41.01 | 50.29 | 24.58 |

TABLE 7-continued

Reaction of α,ω-alkanol amines

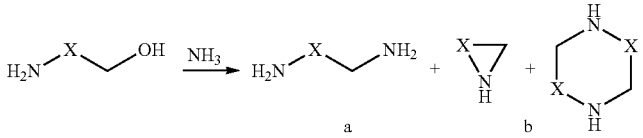

| No.[a] | Alcohol | Solvent (waterfree) | catalyst | T [° C.] | Time [h] | $NH_3$ [eq][d] | Reaction pressure [bar] | Conversion[b] [%] | Selectivity[c] a [%] | Selectivity[c] b [%] |
|---|---|---|---|---|---|---|---|---|---|---|
| 4 | monoaminoethanol | Toluol | XIVb | 155 | 15 | 6 | 42.3 | 72.86 | 69.39 | 12.28 |
| 5 | monoaminoethanol | Toluol | XIVb | 180 | 12 | 6 | 71.5 | 95.92 | 66.17 | 19.25 |

[a]conditions unless indicated otherwise: 50 ml of solvent, batch size 25 mmol of alkanol amine, 0.1 mol % of catalyst complex XIVb (per alcohol group);
[b]evaluation by GC (% by area);
[c]product selectivity determined by GC,
[d]molar equivalents of $NH_3$ per OH function on the substrate;
[d]batch size: 50 mmol in 300 ml-autoclave

The invention claimed is:

1. A process for preparing a primary amine comprising a functional group of formula (—$CH_2$—$NH_2$) and a further primary amino group by alcohol amination, the process comprising reacting a starting material having a functional group of formula (—$CH_2$—H) and a further functional group (—X), with ammonia with elimination of water, wherein (—X) is selected from the group consisting of a hydroxyl group and a primary amino group, and the reacting is homogeneously catalyzed in the presence of a complex catalyst comprising an element selected from groups 8, 9 and 10 of the Periodic Table and also a donor ligand, wherein the complex catalyst has formula I:

I

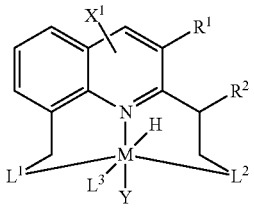

wherein $L^1$ and $L^2$ are each independently selected from the group consisting of $PR^aR^b$, $NR^aR^b$, sulfide, SH, S(═O)R, $C_5$-$C_{10}$-heteroaryl comprising at least one heteroatom selected from the group consisting of N, O and S, $AsR^aR^b$, $SbR^aR^b$ and an N-heterocyclic carbene of formula II or III:

(II)

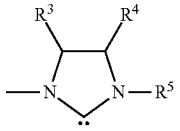

-continued (III)

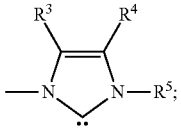

$L^3$ is a monodentate two-electron donor selected from the group consisting of CO, $PR^aR^bR^c$, $NO^+$, $AsR^aR^bR^c$, $SbR^aR^bR^c$, $SR^aR^b$, RCN, RNC, $N_2$, $PF_3$, CS, pyridine, thiophene, tetrahydrothiophene and an N-heterocyclic carbene of formula II or III;

$R^1$ and $R^2$ are both hydrogen or together with carbon atoms to which they are bound form a phenyl ring which together with the quinolinyl unit of formula I forms an acridinyl unit;

R, $R^a$, $R^b$, $R^c$, $R^3$, $R^4$ and $R^5$ are each independently unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from the group consisting of N, O and S, $C_5$-$C_{10}$-aryl or $C_5$-$C_{10}$-heteroaryl comprising at least one heteroatom selected from the group consisting of N, O and S, wherein substituents are selected from the group consisting of F, Cl, Br, OH, CN, $NH_2$ and $C_1$-$C_{10}$-alkyl;

Y is a monoanionic ligand selected from the group consisting of H, F, Cl, Br, I, OCOR, $OCOCF_3$, $OSO_2R$, $OSO_2CF_3$, CN, OH, OR and $N(R)_2$, or an uncharged molecule selected from the group consisting of $NH_3$, $N(R)_3$ and $R_2NSO_2R$;

$X^1$ represents one, two, three, four, five, six or seven substituents on an atom of the acridinyl unit or one, two, three, four or five substituents on an atom of the quinolinyl unit, where plural $X^1$ are selected independently from the group consisting of hydrogen, F, Cl, Br, I, OH, $NH_2$, $NO_2$, —NC(O)R, $C(O)NR_2$, —OC(O)R, —C(O)OR, CN, and a borane derivative that can be obtained from the catalyst of formula I by reaction with $NaBH_4$, and unsubstituted or at least monosubstituted $C_1$-$C_{10}$-alkoxy, $C_1$-$C_{10}$-alkyl, $C_3$-$C_{10}$-cycloalkyl, $C_3$-$C_{10}$-heterocyclyl comprising a heteroatom selected from N, O and S, $C_5$-$C_{10}$-aryl and $C_5$-$C_{10}$-heteroaryl comprising at least one heteroatom selected from the group consisting of N, O and S, wherein substituents are selected from the group consisting of F, Cl, Br, OH, CN, $NH_2$ and $C_1$-$C_{10}$-alkyl; and M is iron, cobalt, nickel, ruthenium, rhodium, palladium, osmium, iridium or platinum.

2. The process according to claim 1, wherein $R^1$ and $R^2$ are both hydrogen and the complex catalyst has formula (IV):

(IV)

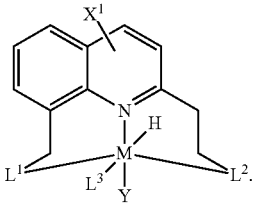

3. The process according to claim 1, wherein $R^1$ and $R^2$ together with carbon atoms to which they are bound form a phenyl ring which together with the quinolinyl units of formula I forms an acridinyl unit and the complex catalyst has formula (V):

(V)

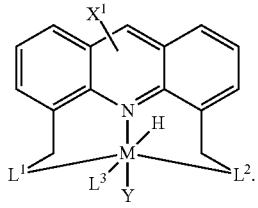

4. The process according to claim 1, wherein the complex catalyst is selected from the group of catalysts of formulae (VI), (VII), (VIII), (IX), (X), (XI), (XII) and (XIII):

(VI)

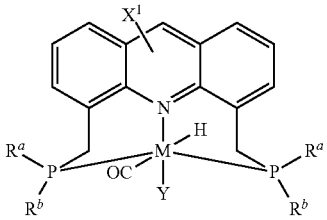

(VII)

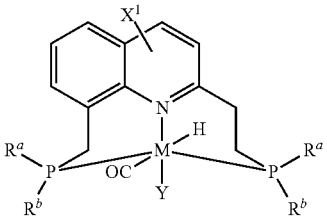

-continued (VIII)

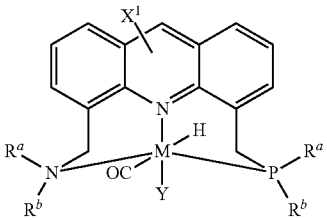

(IX)

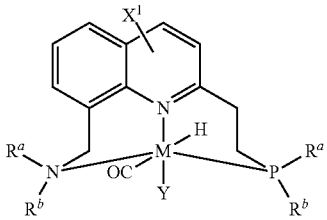

(X)

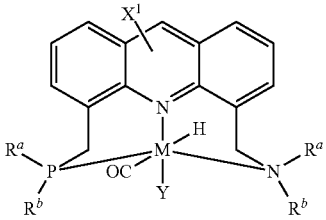

(XI)

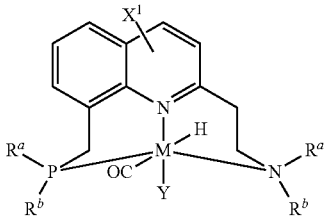

(XII)

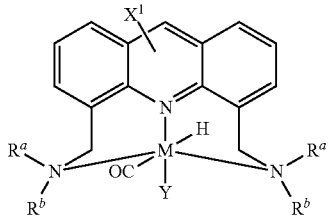

(XIII)

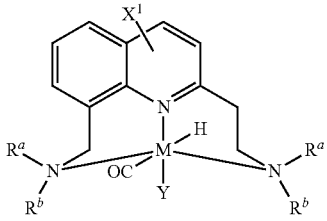

5. The process according to claim 1, wherein the complex catalyst has formula (XIVa):

(XIVa)

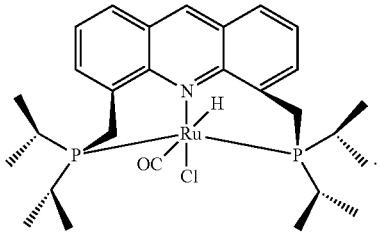

6. The process according to claim 1, wherein the complex catalyst has formula (XIVb):

(XIVb)

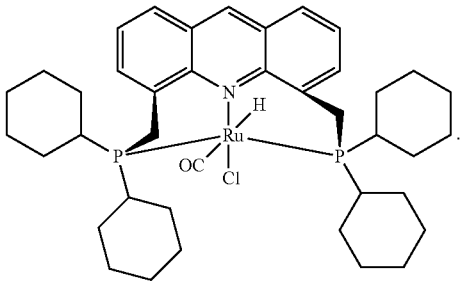

7. The process according to claim 1, wherein the complex catalyst has formula (XV):

(XV)

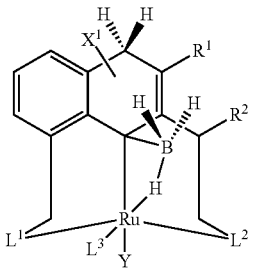

wherein $L^1$ and $L^2$ are each independently selected from the group consisting of $PR^aR^b$, $NR^aR^b$, sulfide, SH, S(═O)R, $C_5$-$C_{10}$-heteroaryl comprising at least one heteroatom selected from the group consisting of N, O and S, $AsR^aR^b$, $SbR^aR^b$ and an N-heterocyclic carbene of formula (II) or (III):

(II)

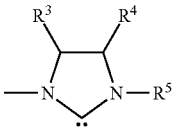

(III)

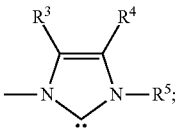

$L^3$ is a monodentate two-electron donor selected from the group consisting of CO, $PR^aR^bR^c$, $NO^+$, $AsR^aR^bR^c$, $SbR^aR^bR^c$, $SR^aR^b$, RCN, RNC, $N_2$, $PF_3$, CS, pyridine, thiophene, tetrahydrothiophene and an N-heterocyclic carbene of formula (II) or (III);

$R^1$ and $R^2$ are both hydrogen or together with carbon atoms to which they are bound form a phenyl ring which together with the quinolinyl unit of formula (XV) forms an acridinyl unit;

R, $R^a$, $R^b$, $R^c$, $R^3$, $R^4$ and $R^5$ are each independently unsubstituted or at least monosubstituted $C_1$-$C_{10}$-alkyl, $C_3$-$C_{10}$-cycloalkyl, $C_3$-$C_{10}$-heterocyclyl comprising at least one heteroatom selected from the group consisting of N, O and S, $C_5$-$C_{10}$-aryl or $C_5$-$C_{10}$-heteroaryl comprising at least one heteroatom selected from the group consisting of N, O and S, wherein substituents are selected from the group consisting of: F, Cl, Br, OH, CN, $NH_2$ and $C_1$-$C_{10}$-alkyl; and $X^1$ represents one, two, three, four, five, six or seven substituents on an atom of the acridinyl unit or one, two, three, four or five substituents on an atom of the quinolinyl unit, where plural $X^1$ are selected independently from the group consisting of hydrogen, F, Cl, Br, I, OH, $NH_2$, $NO_2$, —NC(O)R, C(O)$NR_2$, —OC(O)R, —C(O)OR, CN, a borane derivative that can be obtained from the catalyst of formula (XV) by reaction with $NaBH_4$, and unsubstituted or at least monosubstituted $C_1$-$C_{10}$-alkoxy, $C_1$-$C_{10}$-alkyl, $C_3$-$C_{10}$-cycloalkyl, $C_3$-$C_{10}$-heterocyclyl comprising at least one heteroatom selected from the group consisting of N, O and S, $C_5$-$C_{10}$-aryl and $C_5$-$C_{10}$-heteroaryl comprising at least one heteroatom selected from the group consisting of N, O and S, wherein substituents are selected from the group consisting of: F, Cl, Br, OH, CN, $NH_2$ and $C_1$-$C_{10}$-alkyl.

8. The process according to claim 1, wherein the complex catalyst has formula (XVIa):

(XVIa)

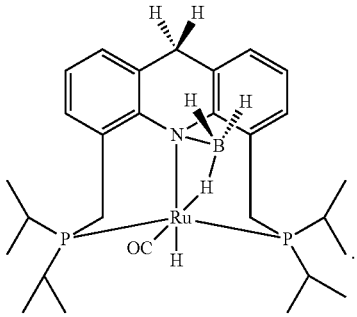

9. The process according to claim 1, wherein Y in the complex catalyst is selected from the group consisting of H, F, Cl and Br.

10. The process according to claim 1, wherein $L^3$ in the complex catalyst is CO.

11. The process according to claim 1, wherein (—X) is selected from functional groups of formulae (—$CH_2$—OH) and (—$CH_2$—$NH_2$).

12. The process according to claim 1, wherein the starting material is diethylene glycol.

13. The process according to claim 1, wherein the starting material is a diol selected from the group consisting of ethylene glycol, diethanolamine, polytetrahydrofuran and 1,4-butanediol.

14. The process according to claim 1, wherein the donor ligand is a phosphorus donor ligand.

15. The process according to claim 1, wherein M is Ru.

16. The process according to claim 1, wherein M is Ir.

17. The process according to claim 1, wherein M is Ru or Ir, and the donor ligand is a phosphorus donor ligand.

18. The process according to claim 1, wherein the starting material is a triol or a polyol.

19. The process according to claim 1, wherein the starting material is at least one triol selected from the group consisting of glycerol, trimethylolpropane and triethanolamine.

*20. The process according to claim 1, wherein the starting material is at least one polyol selected from the group consisting of pentaerythritol, glucose, mannose, fructose, ribose, deoxyribose, galactose, fucose, rhamnose, sucrose, lactose, cellulose, maltose, amylose, xanthan and polyvinyl alcohols.*

* * * * *